US009446288B1

United States Patent
Pazan

(10) Patent No.: US 9,446,288 B1
(45) Date of Patent: Sep. 20, 2016

(54) EXERCISE AND THERAPY DEVICE HAVING SPNRED MATERIAL

(71) Applicant: Steven E. Pazan, Washington, DC (US)

(72) Inventor: Steven E. Pazan, Washington, DC (US)

(*) Notice: Subject to any disclaimer, the term of this patent is extended or adjusted under 35 U.S.C. 154(b) by 176 days.

(21) Appl. No.: 14/166,647

(22) Filed: Jan. 28, 2014

Related U.S. Application Data

(60) Provisional application No. 61/757,531, filed on Jan. 28, 2013.

(51) Int. Cl.
*A63B 24/00* (2006.01)
*A63B 23/035* (2006.01)

(52) U.S. Cl.
CPC ......... *A63B 24/0087* (2013.01); *A63B 23/035* (2013.01)

(58) Field of Classification Search
CPC .................................................. A63B 21/00
USPC ......................................... 482/52, 79, 80, 51
See application file for complete search history.

(56) References Cited

U.S. PATENT DOCUMENTS

| 4,461,472 | A | 7/1984 | Martinez |
| 5,368,535 | A | 11/1994 | Twardokens |
| 6,944,974 | B2 | 9/2005 | Falone et al. |
| 7,468,025 | B2 | 12/2008 | Hauser et al. |
| 2005/0003931 | A1 | 1/2005 | Mills et al. |
| 2011/0124473 | A1 | 5/2011 | Kole et al. |

OTHER PUBLICATIONS

Anne Kavounoudias et al.; "The plantar sole is a dynamometric map for human balance control"; NeuroReport, vol. 9; No. 14; Oct. 1998; pp. 3247-3252.
Keir G. Pearson; "Proprioceptive regulation of locomotion"; University of Alberta, Edmonton, Canada; pp. 786-791, 1995.
Richard Fitzpatrick et al.; "Stable human standing with lower-limb muscle afferents providing the only sensory input"; Journal of Physiology; 1994; pp. 395-403.
J.H.J. Allum; "Age-dependent variations in the directional sensitivity of balance corrections and compensatory arm movements in man"; Journal of Physiology; 2002; pp. 643-663.
Y.P. Ivanenko; "Influence of Leg Muscle Vibration of Human Walking"; The American Physiological Society; 2000; pp. 1737-1747.
A. L. Mattes, "Active Isolated Stretching," 2012, 20 pages, pp. 65-68, 74-75, 78, 79, 81-85, 95-97.
"Victoryturf / Victoryturf 10MM," Shaw Sportexe, 2010, 4 pages.
Firm Grip Resistance Forearm Strength Trainer, Herrington Catalog.com, Jan. 21, 2013, 2 pages.
"Foot Exercises," EXSC 6203, Spring 2012, 1 page.
A. L. Mattes, "Active Isolated Stretching: The Mattes Method," Jan. 28, 2013, 7 pages, pp. 80-85.

(Continued)

*Primary Examiner* — Jerome W Donnelly
(74) *Attorney, Agent, or Firm* — Blank Rome LLP

(57) ABSTRACT

An exercise/therapy device has a base, a foot receptacle rotatably mounted to the base, and one or more rollers mounted to the base and aligned with the foot receptacle. Somatosensory proprioceptive neuromuscular re-education (SPNRED) material is provided on the foot receptacle and/or rollers to stimulate the user's foot during exercise. The exercise device allows for Active Isolated Stretching by enabling multiple exercises and stimulation materials that can be quickly interchanged.

19 Claims, 25 Drawing Sheets

(56) References Cited

OTHER PUBLICATIONS

D-Y Jung et al., "A Comparison in the Muscle Activity of the Abductor Hallucis and the Medical Logitudinal Arch Angle During Toe Curl and Short Foot Exercises," Physical Therapy in Sport, vol. 12, 2001, pp. 30-35.

S. E. Robbins et al., "Running-Related Injury Prevention Through Barefoot Adaptations," Medicine and Science in Sports and Exercise, vol. 19, No. 2, 1987, pp. 148-156.

W. Potthast et al., "Changes in Morphology and Function of Toe Flexor Muscles are Related to Training Footwear," 2005, 2 pages.

D. Goldreich et al., "Tactile Acuity is Enhanced in Blindness," The Journal of Neuroscience, vol. 23, No. 8, Apr. 15, 2003, pp. 3439-3445.

P. M. Kennedy et al., "Distribution and Behaviour of Glabrous Cutaneous Receptors in the Human Foot Sole," Journal of Physiological Society, vol. 538, No. 3, 2002, pp. 955-1002.

"Modeling the Somatotopic Map," 1984, pp. 101-117.

T. Elbert et al., "Increased Cortical Representation of the Fingers of the Left Hand in String Players," Science, vol. 270, No. 5234, Oct. 13, 1995, pp. 305-307.

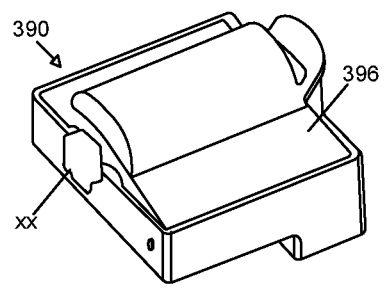 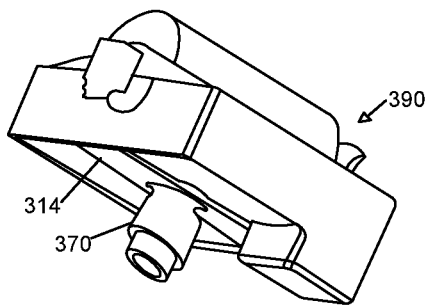
FIG. 9A  FIG. 9B
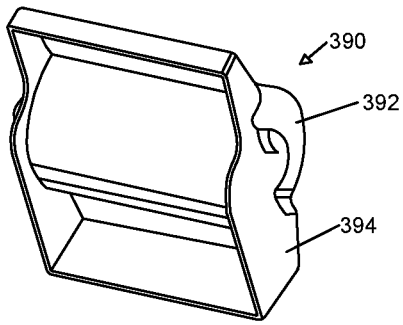
FIG. 9C

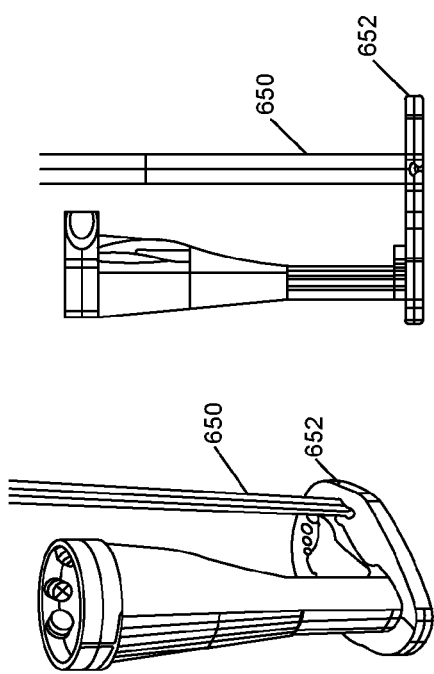
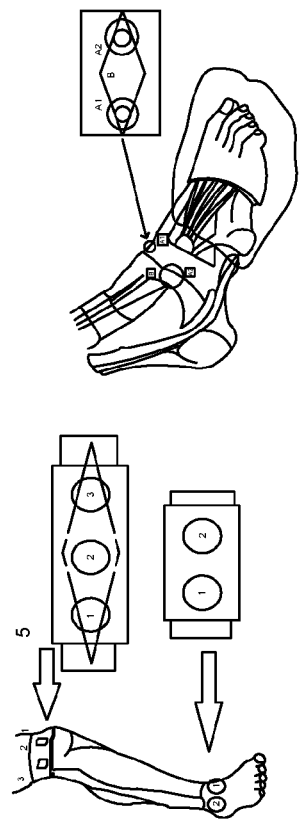
FIG. 11B
FIG. 11D
FIG. 11A
FIG. 11C

EXERCISE AND THERAPY DEVICE HAVING SPNRED MATERIAL

RELATED APPLICATIONS

This application claims the benefit of U.S. Provisional Application No. 61/757,531, filed Jan. 28, 2013, the entire contents of which are incorporated herein by reference.

BACKGROUND OF THE INVENTION

1. Field of the Invention

The present invention relates to an exercise and therapy device. More particularly, the present invention relates to a device that provides exercise and therapy to a user.

2. Background of the Related Art

The brain area that is responsible for our sense of touch is called the somatosensory cortex. Hand and face regions are considerably more densely provided with touch receptors than the skin on the arms and on the trunk and therefore have a much larger image area in the somatosensory cortex. The neural projections are not rigid, but can change under the nuances of sensory experience or as the result of a loss of sensory input, e.g., after nerve damage. The necessary modifications of the connections between receptors and sensory neurons are thought to be, at least in part, activity driven. For example, experiments have revealed that frequent stimulation of skin regions leads to an expansion of their representation in the somatotopic map. (Jenkins et al., Chap. 7, Modeling the Somatotopic Map, pp. 101-117, 1984). Conversely, neurons whose receptors no longer receive any stimuli become sensitive to other receptors which are still active. (Kaas et al. 1983).

People who exercise their tactile abilities have an expanded representation of the trained body part in primary somatosensory cortices. For instance, Braille readers show superior tactile abilities as a group, and have enlarged somatosensory representation of the right index finger, which is used in Braille reading, compared to the left index finger, which was not used in reading. (Pascual-Leone & Torres, 1993). Likewise, professional string players have tactile stimulation of left hand digits, which elicited a larger and enhanced activation in somatosensory input corresponding regions. (Ebert et al., "Increased Cortical Representation of the Fingers of the Left Hand in String Players." SCIENCE 270 (1995), 305).

Somatosensory input from the lower limb has long been recognized as an important source of sensory information in controlling standing balance. (Fitzpatrick, R., Rogers, D. K. & McCloskey, D. I. (1994). Stable human standing with lower-limb muscle afferents providing the only sensory input. Journal of Physiology 480, 395-403; Allum, J. H. J., et al. "Age-dependent variations in the directional sensitivity of balance corrections and compensatory arm movements in man." The Journal of physiology 542.2 (2002): 643-663). In addition, proprioceptive information from muscle spindles in muscles from around the knee and ankle may change joint angle relative to the trunk (Ivaneko, Y. P., Grasso, R. & Lacquaniti, F. (2000). Influence of leg muscle vibration on human walking. Journal of Neurophysiology 84, 1737-1747), while Golgi tendon organs may be responsible for force feedback about the loading of the body. (Pearson, K. G. (1995). Proprioceptive regulation of locomotion. (Review). Current Opinion in Neurobiology 5, 786-791). Finally, skin receptors in the foot sole are sensitive to contact pressures (Magnusson, M., Enbom, H., Johansson, R. & Pyykko, I. (1990). Significance of pressor input from the human feet in anteriorposterior postural control. The effect of hypothermia on vibration-induced body-sway. Acta Oto-Laryngolica 110, 182-188.) and may be sensitive to potential changes in the distribution of pressure. (Kavounoudias, A., Roll, R. & Roll, J. P. (1998). The plantar sole is a 'dynamometric map' for human balance control. NeuroReport 9, 3247-3252). Together, the integration of all these somatosensory inputs appears to provide important information about the body's position with respect to the supporting surface.

A wide variety of exercise devices exist to build strength of the user. These devices generally focus on increasing muscle strength, such as the abdomen, pectorals or biceps. In addition, therapeutic devices have been developed that build strength or increase flexibility to assist with the rehabilitation of a patient who has suffered an injury or medical procedure. There are currently a few exercise devices that have been developed to challenge the foot in a strength training way, such a shown in U.S. Pat. Nos. 4,461,472, 5,368,535 and U.S. Publ. No. 2011/0124473. However, there are no devices are known that exercise, stimulate, and train the somatosensory, proprioceptive neuromuscular re-education (SPNRED™) pathways that focus on digital movements (toes and fingers).

Over the past few decades many experts have advocated that stretching should last up to 30-60 seconds. However, prolonged static stretching actually decreases the blood flow within the tissue creating localized ischemia and lactic acid buildup. This can potentially cause irritation or injury of local muscular, tendinous, lymphatic, as well as neural tissues, similar to the effects and consequences of trauma and overuse syndromes. Performing an Active Isolated Stretch (AIS) of no longer than two seconds allows the target muscles to optimally lengthen without triggering the protective stretch reflex and subsequent reciprocal antagonistic muscle contraction as the isolated muscle achieves a state of relaxation. These stretches provide maximum benefit and can be accomplished without opposing tension or resulting trauma. Using a 2.0 second stretch has proven to be the key in avoiding reflexive contraction of the antagonistic muscle. Without activating muscle group contraction, restoration of full range of motion and flexibility can be successfully achieved. (Aaron Mattes, www.stretchingusa.com; Sherrington, C. S., Proc. Boy. Soc, 1897, 60, 414-417; Sherrington, C. S. The integrative action of the central nervous system, Yale University Press. 411 pp.; Sherrington, C. S., and Hering, E. S. Antagonistic muscles and reciprocal innervation. Fourth note. Pi-oc Boy. Soc, 1898, 62, 183-7).

Active Isolated Strengthening, Aaron Mattes Method 2006, Towel exercises Foot exercises pages 121 and 122, Foot Flexion, 1st, Supination, 2nd, Pronation 3rd. Citing Aaron Mattes' Active Isolated Strengthening: The Mattes Method (2006), we have identified and categorized these as non-weight bearing accessory exercises which is non-discriminatory (age/gender), versatile, and assists within varying types of exercise regimen (rehabilitative, season, or sport specific training). The three exercises are foot Pronation, Supination, and foot Flexion. As stated by Mattes (2006), these exercises are designed to help build arch strength, rehabilitate postoperative or post injury foot-ankle problems. The purpose is to strengthen the intrinsic muscles of the feet (Mattes, 2006). All three exercises utilize a towel as a tool to increase foot sensation and contact surface orientation and the use of a weight as resistance. The novel exercises train the coupled motions of the foot and ankle (talocrural, subtalar, and tarsometatarsal) joints: to increase range of motion (ROM) and strength when performing eversion and inversion, abduction and adduction, supination and pronation, dorsiflexion and plantar flexion. In addition they also train the toes (MPJ): flexion and extension, and abduction and adduction. Directly isolating and strengthening these movements while using neuromuscular proprioceptive techniques is an effective training style. The exercises are intended to mimic ankle movements during weight bearing activity but allow for isolated strengthening of the intrinsic musculature through progressive overload.

Research has shown that variations of the three novel exercises have been used to strengthen the intrinsic foot musculature. Jung et al. (2011) confirmed that the towel curl exercise is used to strengthen the Flexor Digitorum Longus (FDL) and Brevis (FDB), Lumbricales, and Flexor Hallucis Longus (FHL), (Jung D Y, Kim M H, Koh E K, Kwon O Y, Cynn H S, and Lee W H. (2011). A comparison in the muscle activity of the abductor hallicus and the medial longitudinal arch angle during toe curl and short foot exercise, Physical Therapy in Sport 12: 30-35, 2011). Potthast et al. supports these exercises because each exercise has an effect on toe flexion. (Potthast, et al., The Choices of Training Footwear Has an Effect on Changes: In Morphology and Function of Foot and Shank Muscles. 23 International Symposium on Biomechanics in Sports. Beijing-China, Aug. 22-27, 2005 (2005)). Toe flexion plays a large role in the training and maintenance of the transverse and both longitudinal arches. Robbins & Hanna (1987) support these exercises by previously stating that intrinsic muscles of the foot are responsible for maintaining the longitudinal arches of the foot. (Robbins, S., Hanna, A., (1987). Running-related injury prevention through barefoot adaptations. Medicine and Science in Sports and Exercise. 19(2): 148-156.)

Training inversion, the combination of plantar flexion, supination, and adduction, will train and maintain the Medial Longitudinal arch of the foot. Potthast et al. (2005) concluded that the increase in Plantar Flexion and Inversion strength in the experiment can be explained by the functional adaptations and ACSA of FHL and FDL. The evidence on Inversion training can be extrapolated to Eversion isolated training. Training Eversion, which is a combination of Dorsi Flexion, Pronation, and Abduction will train and maintain the Lateral Longitudinal arch of the foot. Properly training the intrinsic musculature of the lower extremity in a proprioceptive manner will stimulate the sensory receptors of the foot. Through strength adaptation pathways, the structures of the foot will become more prepared to withstand new biomechanical forces associated with barefoot activity and minimalist footwear use. (Jung D Y, Kim M H, Koh E K, Kwon O Y, Cynn H S, and Lee W H, A comparison in the muscle activity of the abductor hallicus and the medial longitudinal arch angle during toe curl and short foot exercise, Physical Therapy in Sport 12: 30-35, 2011; Potthast et al. (2005), The Choices of Training Footwear Has an Effect on Changes; In Morphology and Function of Foot and Shank Muscles. 23 International Symposium on Biomechanics in Sports. Beijing, China, Aug. 22-27, 2005; Robbins, S., Hanna, A., (1987), Running-related injury prevention through barefoot adaptations, Medicine and Science in Sports and Exercise, 19(2): 148-156).

SUMMARY OF THE INVENTION

Accordingly, it is an object of the invention to provide an exercise device that functionally exercises, stimulates, and thusly trains the somatosensory, proprioceptive neuromuscular re-education (SPNRED™) like pathways. It is a further object of the invention to provide an exercise device that focuses on digital movements (toes and fingers), such as dexterity in addition to the palmar and plantar surfaces for hand and foot respectively which have sensory receptors that are unique to those areas such as glabarous skin receptors, muscle spindles, golgitendon organs, etc. It is a further object of the invention to provide an exercise device that includes digital movement for the toes or fingers.

It is a further object of the invention to provide an exercise device that couples SPNRED materials to positively affect AIS (Active Isolated Stretching), which improves form and function of both the upper and lower extremities to assist and/or improve musculoskeletal injury rehabilitation, injury prevention, sports performance, and quality of life, such as by increasing strength, flexibility, and sensori-motor training. Training these receptors and associated afferent and efferent pathways within the body through the use of somatosensory proprioceptive neuromuscular re-education (SPNRED) material application and associated exercises improves sensory receptor use, timing, identification, neuromuscular reactions and pathways, foot balance and associated hand technical application qualities of the user.

In accordance with these and other objectives of the invention, an exercise/therapy device that incorporates SPNRED stimulatory materials and can be used for flexibility training of the extremities, such as by AIS, PNF (proprioceptive neuromuscular facilitation), static, dynamic, ballistic, passive, active, or isometric stretching. The device receives the user's foot and enables the user to rotate the foot while simultaneously scrunching and laterally moving the toes. The motion stimulates SPNRED to increase strength and flexibility.

These and other objects of the invention, as well as many of the intended advantages thereof, will become more readily apparent when reference is made to the following description, taken in conjunction with the accompanying drawings.

BRIEF DESCRIPTION OF THE FIGURES

FIGS. 9A-C show another embodiment for the roller;

FIG. 10A is a top view, FIG. 10B is a perspective view, FIG. 10C is a side view, FIG. 10D is an exploded view, and FIG. 10E shows a single foot receptacle;

FIGS. 11A-E show a foot strap in accordance with an alternative embodiment of the invention;

DETAILED DESCRIPTION OF THE PREFERRED EMBODIMENTS

Figure 1:
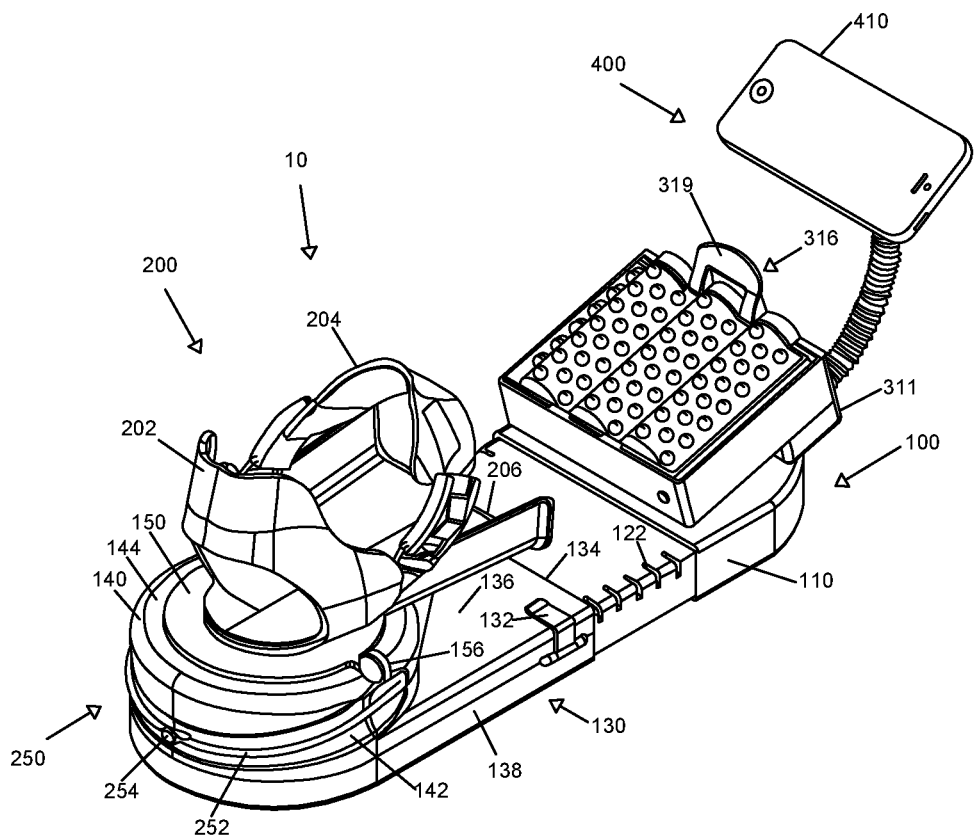
FIG. 1 is a perspective view of the exercise system in accordance with the preferred embodiment of the invention.

In describing a preferred embodiment of the invention illustrated in the drawings, specific terminology will be resorted to for the sake of clarity. However, the invention is not intended to be limited to the specific terms so selected, and it is to be understood that each specific term includes all technical equivalents that operate in similar manner to accomplish a similar purpose. Several preferred embodiments of the invention are described for illustrative purposes, it being understood that the invention may be embodied in other forms not specifically shown in the drawings.

Figure 2:
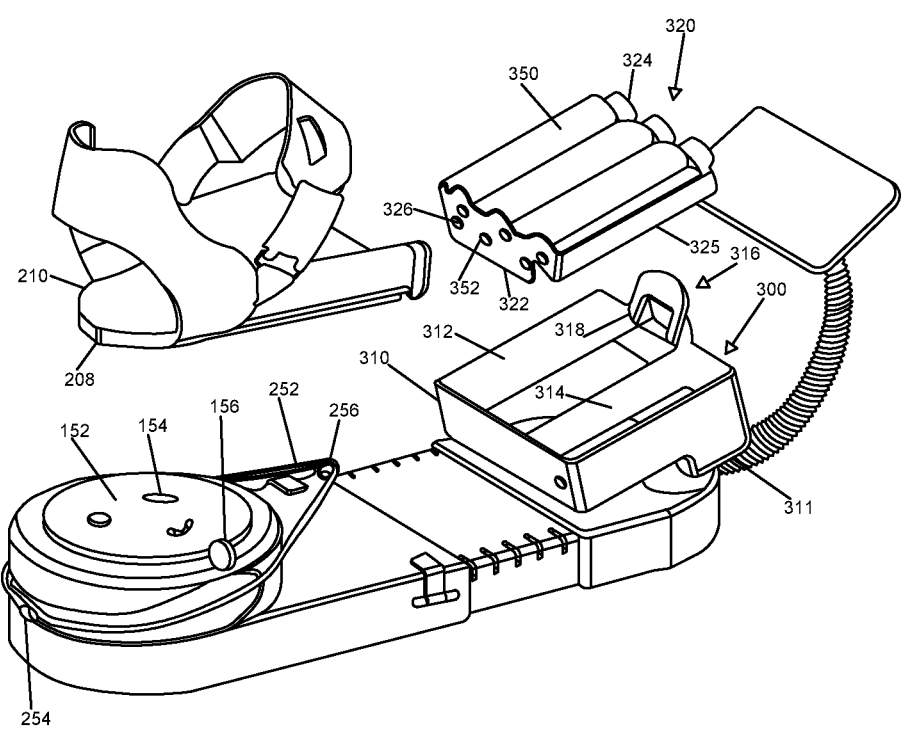
FIG. 2 is an exploded view of the system of FIG. 1.

Turning to the drawings, FIGS. 1 and 2 show the exercise and/or therapeutic device 10 of the present invention. The device 10 can be utilized for exercise and/or therapeutic rehabilitation of a user. As shown, the exercise device 10 generally includes a base 100, foot receptacle 200, resistance mechanism 250, exercise system 300 and tracking system 400. The base 100 provides the general support to the device 10 and attaches the foot receptacle 200 and the exercise system 300, which is a roller system 300 in the present embodiment. The foot receptacle 200 receives the user's foot and allows the user to rotate his/her foot with respect to the roller system 300. The roller system 300 provides an exercise for the user, whereby the user can scrunch his/her toes on the rollers 350 and provide a sideways motion to roll the rollers 350 as the user rotates his/her foot in the foot receptacle 200. The resistance mechanism 250 provides resistance to the user's rotational movement to provide a desired level of exercise.

The base 100 has an elongated oblong shape that is slightly larger than a human foot. The base 100 has a front or toe section 110, a mid-section 120 and a rear or heel section 130. The toe section 110 connects with the roller system 300. The mid-section 120 is formed integrally with the toe section 110. Accordingly, that the base 100 is a two-piece member, whereby the toe and mid sections 110, 120 form one piece, and the heel section 130 is the second piece. The mid-section 120 has a top plate and side walls 124 that extend down from the top plate. The mid-section 120 is slightly smaller than the toe section 110 and the heel section 130, and is slidably received by the heel section 130. The mid-section 120 also has a plurality of slots 122 positioned along the longitudinal length of the device 10. The slots 122 are formed in the top plate and into the side walls 124, and cooperate with a hinged locking tab 132 to allow the length of the device 10 to be adjusted.

The heel section 130 has a top plate 136 and an outer circumferential side wall 138 that extends downward from the top plate 136. The heel section 130 has a front portion with a leading edge 134, and a rear portion. At least a portion of the side walls 138 of the heel section 130 at the leading edge 134 has an upward turned lip (not shown) at the inside of the wall 138. The upward turned lip forms a channel that slidably receives the side wall 124 of the mid-section 120. Thus, the length of the device 10 can be adjusted by sliding the mid-section 120 into and out of the heel section 130. The entire mid-section 120 can be received by the heel section 130, so that the toe section 110 is flush with the heel section 130.

The hinged locking tab 132 is positioned toward the leading edge of the front portion. The hinged locking tab is hinged to the side wall 138 of the heel section 130. It is flat and bent at about its middle to form an L-shape with a side and top. The top has a tab (not shown) that extends outward from the inside face of the top. The locking mechanism 132 extends from the side wall 138 to the top surface of the top plate 136. Once the mid-section 120 is adjusted to the desired length within heel section 130, the locking mechanism (hereafter referred to as the lock) 132 is pressed downward so that the tab enters the slot 122 thereby locking the lock 132 in the slot 122. That also locks the heel section 130 with respect to the mid-section 120 and toe section 110, so that the mid-section 120 cannot slide further into or out of the heel section 130. The lock 132 has a slightly upturned distal end, so that the user can pull up on the lock 132 and withdraw the tab from the slot 122 to unlock the lock 132 and slot 122. As best shown in FIG. 2, a locking mechanism 132 can be provided at opposite sides of the heel section 130.

An upright pedestal 140 is provided at the rear portion of the heel section 130. The pedestal 140 is integral with the heel section 130, and extends upward from the top surface of the top plate 136 so that the foot receptacle 200 is elevated and does not contact the top plate 136. The pedestal 140 is circular and has a curved top edge to prevent injury or interference, such as by snagging clothing. A groove or channel 142 is provided along the rear and sides of the pedestal 140 side and the rear side wall 138 of the heel section 130. The channel 142 is a slight recess in the rear and sides of the pedestal 140 side and the rear side wall 138. The groove 142 receives an elastic band 252 and prevents the band 252 from slipping out of the channel 142 and off of the device 10. A swivel plate 150 is provided at the top surface 144 of the pedestal 140. The swivel 150 is rotatably mounted to the top surface 144, such as by ball bearings or the like. The swivel mount is the same as shown and described with respect to the invention of FIG. 10. Thus the swivel 150 can have a top plate, bottom plate, channel and a ball bearing chain received in respective channels in the plates, to permit the top plate to rotate with respect to the bottom plate.

As best shown in FIG. 2, the swivel plate 150 has a top surface 152, openings 154, and a release handle 156. The openings 154 are provided in the top surface 152. The openings 154 have a circular portion and a slot to have a general keyhole shape (though other suitable shapes can be provided). The slot has a width that is smaller than the diameter of the circular portion. The foot receptacle 200 has a mating connector or pin 208 that is received in the openings 154. The pin 208 has a circular body and a wide circular head that is larger than the circular body. The head of the connector 208 is slightly smaller than the circular portion of the openings 154, and slightly larger than the slot portion of the openings 154. The body of the pin 208 is slightly smaller than the slot portion of the openings 154. Accordingly, the head of the pin 208 is received in the circular portion and plate 150 or foot receptacle 200 is rotated so that the body portion slides into the narrow slot of the opening 154. This locks the foot receptacle 200 to the swivel plate 150 since the large head of the pin 208 cannot pull directly upward out of the slot portion of the opening 154.

The release 156 is connected to the swivel plate 150 and forms a handle that extends outward from the swivel plate 150. The release 156 enables the user to rotate the swivel plate 150 to control the locking and unlocking by moving the swivel plate 150 and openings 154 with respect to the foot receptacle 200 and the connector 208. The user can also use the release 156 to hold the swivel plate 150 steady so that the foot receptacle 200 can be rotated to control locking and unlocking.

Figure 3:
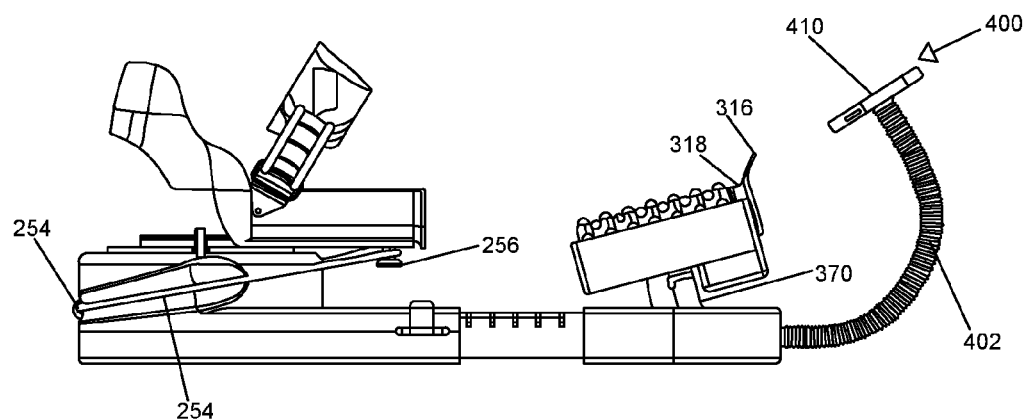
FIG. 3 is a side view of the system of FIG. 1.

As further shown in FIGS. 1-3, the foot receptacle 200 is a single piece element that includes a heel 202, strap 204, and sole plate or platform 206. The heel 202 is formed by a strap chat extends across the rear portion of the foot receptacle 200 and supports the heel of the user when the device 10 is being utilized. The strap 204 extends across the top of the user's foot and secures the foot to the foot receptacle 200 with the user's heel against the heel 202. The platform 206 receives and supports the user's sole. The platform 206 extends only a portion of the user's sole from the heel, so that the user's toes and the front portion of the user's foot are free to move about. The platform 206 has upwardly-turned sides to prevent the foot from sliding out of the foot receptacle 200 and to provide comfort to the user. However, the front end of the platform 206 is not turned upwardly, so that the user's foot can extend outward from the receptacle 200. The platform 206 can be flared out slightly so that there are no edges that might otherwise injure the user.

In addition, the top surface of the platform 206, the bottom surface of the foot strap 204, and the inside surface of the heel 202, are all coated or layered with a proprioceptive material 210 (FIG. 2). The proprioceptive or SPNRED materials 210 provide sensory stimulation to the user's foot during exercise, which in turn increases the afferent and efferent signaling throughout the motor-cortex and kinetic chain. For the foot, the toes and palmar aspects of the sole of the foot provide imperative information regarding the surface at which the user is standing on. By challenging and training the user to feel different materials under the foot, the foot-user-feedback system is improved. This improvement allows for the user either normal, special population, or athlete be capable of having more "kinesthetic" awareness thus improving their balance and reaction timing. This improves balance, gait mechanics, sports specific activities, reaction timing, fluidity of movements among other gross and finite movements provided by the foot/ground interface. The tactile contact with the SPNRED material improves muscle strengthening during use of the device. The same will go for the upper body but besides providing balance the user will gain an improvement in their hands, finger, and grip for function ranging from grabbing a railing or assistive device (suggested but not limited to walkers, canes, scooters, powered and unpowered wheel chairs while walking to gripping a glass/mug, utensils, to utilizing keys.

For purposes of providing a non-limiting illustration of the invention, the proprioceptive material 210 can have a base layer formed by an aramid weave, including an aramid weave such as KEVLAR® by DUPONT® to support the proprioceptive material 210 by providing stiffness to the underbelly of the material. The base layer is optional and is particularly suited to the platform 206 of the foot receptacle 200, but is not used for the rollers 350. Other suitable alternatives can also be used, such as but not limited to KEVLAR-like materials, Plastics, Metals, Carbon Fiber, Dyneema, Organic and in-organic material, or as provided in U.S. Pat. No. 6,944,974, which are all incorporated herein by reference.

The base layer is attached by adhesives and/or sewing techniques to the foams consisting of but not limited to closed celled and/or opened celled medical grade or consumer grade foams. The foams attached with the KEVLAR create a stiffer bond when then attached to the Somatosensory Proprioceptive Neuromuscular Re-Educational Material (SPNRED). The combination of the foams and Kevlar provide a shock attenuation factor within the materials structure that re-distributes forces throughout the material. This complements the user's foot when exercising to thus re-distribute ground reaction forces throughout the material during closed chained exercises. This is for comfort purposes to prevent pain from impact during long duration, repetition, within the training timeline. To prevent large amounts of ground reaction forces causing pain or injury to the user during exercise.

In one illustrative embodiment, an aramid weave fiber with a pliable application is used to securely attach to the SPNRED material 210. In the embodiment shown, the proprioceptive material 210 is a very coarse artificial turf, such as LEGEND™ made by Shaw SPORTEX® Synthetic Grass, 2-2.25 inch pile height. However, other varying styles and weaves (coarse or not) of the turf can be utilized. Re-purposing the space where the backfill of coarse rubber pellets and the sand provides space for the fibers within the turf specifically make it ideal for grabbing and stimulating individual toes and or fingers. The LEGEND™ turf is made for outdoor sports with the need for backfill to fill that space. The use of indoor style turf called VICTORYTURF has limited spacing and a tighter packed weave. This higher density of fibers/in$^2$ provides more stimulation/resistance for the place where the user's foot is attached to said devices. The palmar and plantar surfaces of the hands and feet are where the higher stimulation occurs. Other suitable materials can be used, such as animal skins, hair, and rubber filaments. The use of the indoor higher density material can also be used within the scrunching and flicking actions within the finger and toe flexion, extension, abduction, and adduction movements. The use of the higher density weaved materials provide more surface area and contact area within the digits to provide maximum stimulation. The strong coarse fibers provide structure for the ambulation and grabbing motion. Creating the connection, both sensory and physically, enables the user to engage more within the exercise. In an alternative embodiment, the platform 206 can be a layer of rigid material, with a padding layer and a proprioceptive layer 210 positioned over the rigid layer. Though specific turf is discussed here, it will be appreciated that any turf or similar material can be used. It should be understood that the term "turf" as used here, is not limited to a grass-like structure and can be any shape or structure such as flowers or the like in addition to the materials discussed throughout.

As best shown in FIG. 3, a resistance pin 256 is located at the front end of the platform 206 and extends outward and downward from the underside of the platform 206. The resistance pin 256 has a circular body and a wide circular head that is wider than the body to forma lip between the head and the body. In addition, as best shown in FIG. 1, a fastener 254 is positioned at the distal rear end of the device 10. The fastener 254 extends through an opening in the resistance band 252 to affix the resistance band 252 to the rear section 130 of the device 10. As best shown in FIG. 2 (with the foot receptacle 200 removed but the resistance pin 256 still in the position it occupies when attached to the bottom of the platform 206 for purposes of illustration only), the resistance band 252 is a loop that extends from the distal rear of the rear end section 130, forward within the recess guide channel 152, around the roller pin 256. The resistance band 252 can slide back and forth on the resistance pin 256 as the user rotates the foot receptacle 200 left and right with respect to the base 100.

The resistance band 252 provides a desired resistance to the rotational movement of the foot receptacle 200 with respect to the base 100. Different bands can be utilized to provide different amounts of resistance. It should also be appreciated that the resistance band 252 can be fixed to the foot receptacle 200, or instead a resistance can be provided at the swivel 150 so that the rotation of the swivel 150 provides a predetermined resistance to the rotation of the foot receptacle 200 with respect to the base 100.

Still referring to FIGS. 1-3, a roller system 300 is provided at the front section 110 of the exercise/therapeutic device 10. The roller system 300 includes a housing 310, a roller cassette 320 and a support post 370 (FIGS. 3, 9B). The roller housing 310 has a generally rectangular shape with four sides 312 and a bottom panel 314. The bottom 314 need not be entirely closed, but can have a single elongated panel that extends from one side to an opposite side to prevent the roller cassette 320 from slipping through the housing 310. A locking clip 316 extends upward from the top of the front side 312 of the housing 310. The clip 316 includes a pair of lips 318 connected together by a handle 319. The housing 310 can also include an area 311 to house a sensor that detects and measures the movement of the rollers 350. The sensor housing area 311 can be provided at the front of the housing 310, or at the rear or sides, as may be suitable. It should be appreciated that the locking clip 316 can alternatively extend from the side of the housing 310 or the back of the housing 310 (below the foot).

Turning to FIG. 2, the roller cassette 320 has a housing or frame 322, and one or more rollers 350. The roller cassette frame 322 has a generally rectangular shape with a front side 324, left/right sides 325 and a rear side 326. The rollers 350 are cylindrical, such that they are elongated with a circular cross-section. The rollers 350 extend parallel to one another and are aligned so that the rollers 350 can be rotated left/right by the user's toes/foot. Thus as shown, the longitudinal axes of the rollers 350 are substantially parallel to the Longitudinal axis of the foot receptacle 200 platform 206 when the platform 206 is centered. Accordingly, the rollers 350 extend from the front side 324 of the roller frame 322 to the rear side 326 of the frame 322. A pin 352 extends through the center of each of the rollers 350 and connects to the frame 322 through respective openings in the front/rear sides 324, 326 of the cassette frame 322. The pins 352 can freely rotate within the openings in the frame 322. The rollers 350 are fixed to the pins 352 (such as by adhesive, solder, fastener or the like), so that the rollers 350 spin/rotate with respect to the roller frame 322. The roller pins 352 have a widened head so that the pins 352 do not come free from the roller cassette frame 322, thereby rotatably affixing the rollers 350 to the frame 322. Of course, other suitable methods can be used, such as the roller 350 can rotate with respect to the pins 352.

The roller cassette 320 can be removably and lockably received in the housing 310. The roller cassette frame 322 is slightly smaller than the roller housing 310 of the roller system 300 so that the cassette frame 322 can fit inside and be received by the housing 310 of the roller system 300. The rear side 326 of the roller frame 322 is angled into the housing 310 and engages the bottom panel 314 of the housing 310. The front side 324 of the roller cassette frame 322 is then pressed down. The front side 324 comes into contact with the lock 316. As the user presses down on the roller cassette 320, the front side of the housing 324 slides along the angled arms of the lock 316 and push the lock 316 outward. Once the roller cassette 320 is fully inserted in the housing 310, the locking clip 316 snaps (by being biased inward) back over the top of the roller cassette 320, thereby locking the roller cassette 320 to the housing 310. To remove and/or replace the roller cassette 320, the user presses outwardly on the handle 319 of the locking clip 316 and lifts the roller cassette 320 out of the housing 310. It should be appreciated that the orientation for locking would vary if the locking clip 316 alternatively extends from the side of the housing 310 or the back of the housing 310 (below the foot).

As best shown in FIGS. 3 and 9B, the support post 370 extends upward from the top surface of center of the front section 110 and connects with the roller cassette 320. The support post 370 is at a slight angle with respect to the top surface of the base 100, so that the roller cassette 320 is also at an angle with respect to the top surface of the base and also with respect to the foot receptacle 200 and particularly the platform 206. In the embodiment of FIG. 9B, the post 370 connects to the bottom facing surface of the cross-support at the bottom 314 of the housing 310. A post extends downward from the bottom panel 314 with a small projection that engages a channel in the post 370. The post 370 is turned so that the projection enters a bend in the channel to lock the projection in the channel. However, the post 370 can connect with the bottom panel 314 in any suitable manner, such as a fastener, solder or adhesive.

Figure 4:
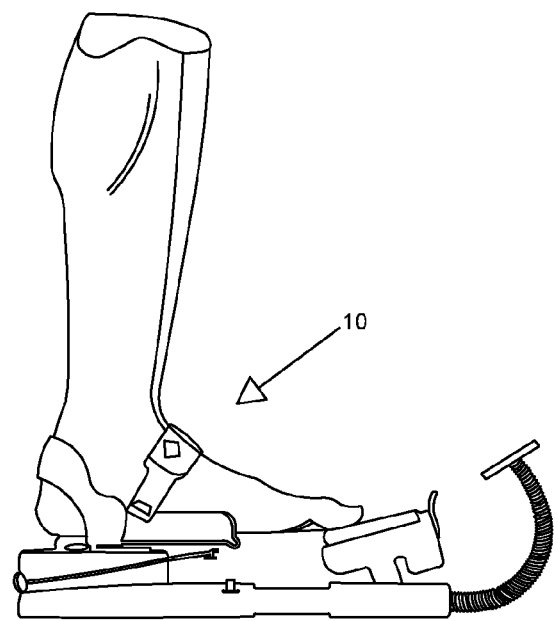
FIG. 4 is a side view of the system of FIG. 1 showing the positioning of a user's foot.

As shown in FIG. 4, the bottom of the rollers 350 are slightly below the platform 206 and the top of the rollers 350 are slightly above the platform 206. Accordingly, the user's toes are best vertically aligned toward the middle of the rollers 350. The post 370 can be adjusted vertically up/down to provide the desired level for the user. And the front section 110 and rear section 130 can be adjusted horizontally forward/back so that the user's toes reach the desired portion of the rollers 350.

As further illustrated in FIG. 3, the foot receptacle 200 and roller system 300 are elevated from the top surface of the base 100. In this way, the base 100 does not interfere with operation of the foot receptacle 200 and/or roller system 300. And, the heights of the foot receptacle 200 and roller system 300 can be controlled to provide a desired alignment of those elements for proper movement of the user.

Still referring to FIG. 3, the monitoring and/or tracking system 400 includes a flexible elongated arm 402 that extends forward from the distal front end of the base 100. A proximal side of the flexible arm 402 extends from the front side face of the toe section 110 and extends upward. A distal end of the arm 402 has a connector that removably receives the electronic monitoring/tracking device 410. Any suitable connector can be used that allows the tracking device 410 to be connected with the arm 402. The arm 402 is flexible, so that it can be adjustably positioned by the user so that the tracking system 410 is clearly visible to the user.

The monitoring/tracking device 410 can monitor and track the exercise performed by the user. One or more sensors (such as motion sensors, transducers, pressure sensors, etc.) can be positioned with respect to the swivel 150, foot receptacle 200 and/or roller system 300. The sensor can be in wired or wireless communication with the tracking device 410 and provide signals to the tracking device 410 about the exercise being performed. Thus, the tracking device 410 can then monitor the number of repetitions, time of exercise, time of repetitions, calories burned, level of resistance, etc. That information can be provided to a physician or the user, and mapped against prior exercise routines. The level of improvement can also be monitored and reported. In addition, the tracking device 410 can implement a game that is played by operating the exercise device 10 to encourage exercise.

In accordance with one preferred non-limiting illustration of the invention, the tracking device 410 can be a mobile phone in wireless communication with the exercise device 10 sensors, such as by Blue Tooth. The tracking device 410 can also operate by mobile applications, such as to perform scheduling with the physician, and other related functions.

Figure 5:
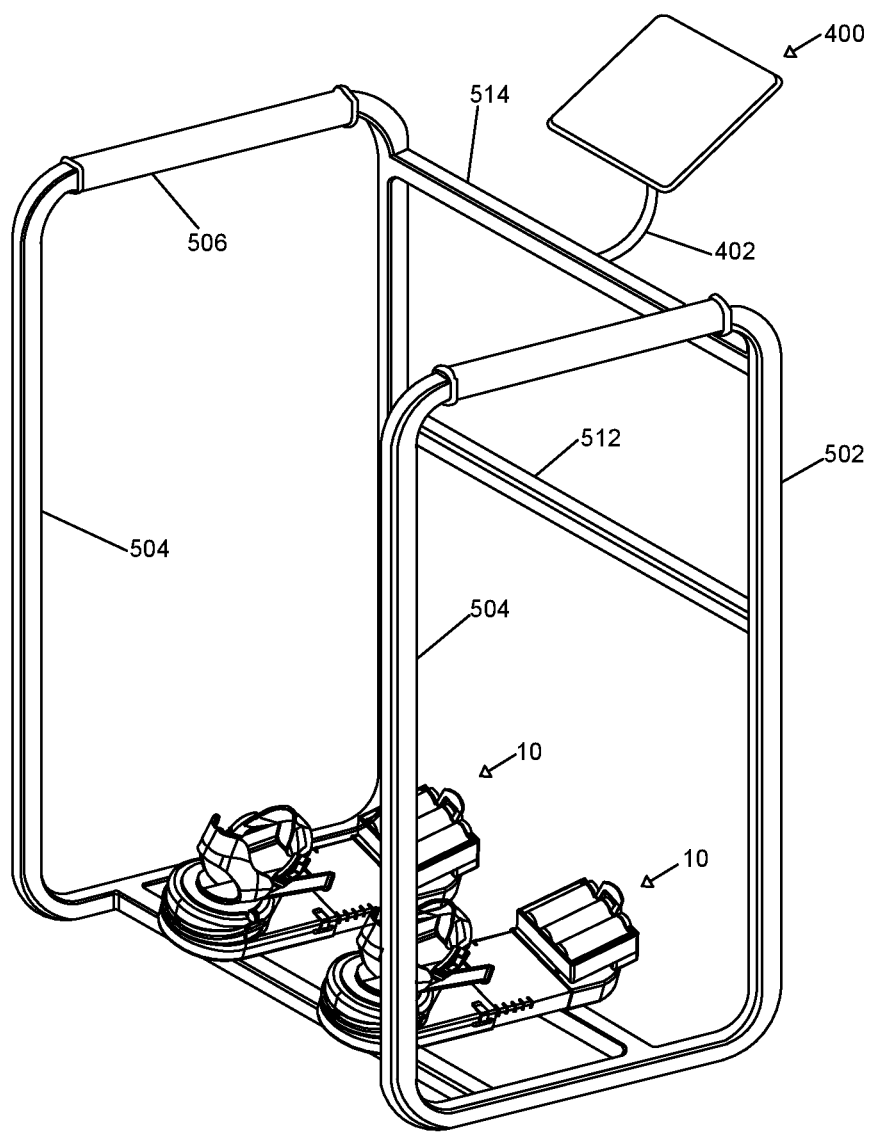
FIG. 5 is a perspective view of the system having a support structure in accordance with another embodiment of the invention.

Turning to FIG. 5, the exercise device 10 can also be mounted to an apparatus 500. The apparatus 500 includes a frame 502 with two sides 504 having a top railing 506 and a bottom railing 508. Two elongated cross-support bars 510 are provided to connect the two bottom railings 508. Lower and upper cross-support bars 512, 514 can be provided to connect the front side bars 504. The exercise device 10 is the same as shown in FIGS. 1-4, except the tracking system 400 (including the arm 402) is attached to the upper front bar 514 and is not directly attached to the exercise device 10. In this embodiment, the user can stand on the two exercise devices 10, using the sides 504 of the frame 502 for stability and/or support.

Figure 6:
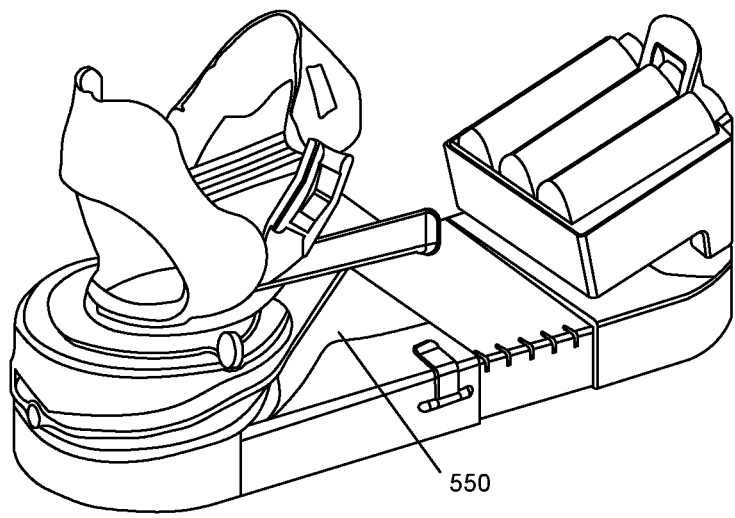
FIG. 6 is a perspective view of the system having weights in accordance with another embodiment of the invention.
Figure 11E:
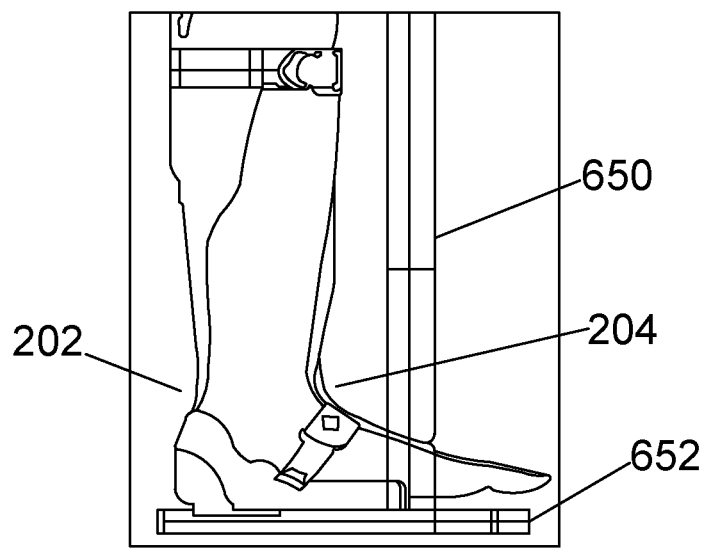

Referring to FIG. 6, another illustrative embodiment of the invention is shown. Here, weights 550 are secured to the foot receptacle 200. The weights can be flat and elongated, and connected to a ledge provided on the outside of the upwardly-turned sides of the foot receptacle 200. The weights 550 increase the resistance of the exercise for the user. The weights can be connected in any suitable manner, such as directly to the outside of the upwardly-turned sides of the platform 206. The device 10 can also be directly mounted to the floor or a platform of a larger device (see for instance, FIGS. 5, 10, 11).

Closed vs Open Chained Activities. Closed Chained Movements occur when the kinetic chain (extremity) is in contact and has some type of weight bearing on or with a surface. Examples include Standing, Squat, Sliding Foot along the floor, Hand Stand, Push Ups, etc. Open Chained Movements occur when the kinetic chain (extremity) is free to move without being weight bearing or stationary. Examples include Knee Flexion and Extension while sitting and their foot is hanging off the side of the table. Standing Hip Flexion, Extension, Abduction and Adduction.

Planes and their associated movements (Anatomical Position) that are exercised by the present invention. Sagital-Flexion and Extension-Frontal-Abduction and Adduction-Transverse-Rotation. Lower Body—Closed Chained Movements within the Sagital, Frontal, and Transverse Plane. Includes Toe Flexion, Extension, Abduction, Adduction; Foot & Ankle Inversion, Eversion, Plantar Flexion, DorsiFlexion; Knee Flexion, Extension, Rotation (Internal and External) Tibial Torsion; Hip Flexion, Extension, Rotation (Internal and External) Femoral Torsion; Upper Body—Closed Chained Movements within the Sagital, Frontal, and Transverse Plane; Finger Flexion, Extension, Abduction, Adduction; Wrist Flexion, Extension, Ulnar and Radial Deviation; Wrist and Elbow—Supination and Pronation; Elbow Flexion, Extension; Shoulder Flexion, Extension, Rotation (Internal and External) Shoulder Rotation.

Lower Body—Open Chained Movements within the Sagital, Frontal, and Transverse Plane that are exercised by the present invention include Toe Flexion, Extension, Abduction, Adduction; Foot & Ankle Inversion, Eversion, Plantar Flexion, DorsiFlexion; Knee Flexion, Extension, Rotation (Internal and External) Tibial Torsion; Hip Flexion, Extension, Rotation (Internal and External) w/(Bent Knee or Straight leg).

The person is enabled to scrunch or swipe the foot, in addition to strengthening the knee or foot. This encompasses strengthening the entire lower body at once. The user can turn the foot during exercising by rotating the base 1 with respect to the turntable 20.

Upper Body—Closed Chained Movements within the Sagital, Frontal, and Transverse Plane that are exercised by the present invention include Finger Flexion, Extension, Abduction, Adduction; Wrist Flexion, Extension, Ulnar and Radial Deviation; Wrist and Elbow—Supination and Pronation; Elbow Flexion, Extension; Shoulder Flexion, Extension, Rotation (Internal and External) w/ Bent Elbow or Straight arm.

The device has no limits to either being used for: Somatosensory Proprioceptive Neuromuscular Training, Balance Training, and Gait Training; Baseline Musculoskeletal Strength and Flexibility Range of Motion Assessments via it being used as a diagnostic tool for evaluation; Occupational & Physical Therapy Training; Pre-habilitation and Rehabilitation (Pre- and Post-Surgical Intervention Care); Injury Rehabilitation; Injury Prevention; Strength and Conditioning Training; Sports Performance including rotational sports (Racquet Sports, Golf, Dance, Martial Arts); Personal Training; Home Exercise Programming.

Rehabilitation Training, Injury Prevention, & Sports Performance include Occupational Therapy—Hand Therapy—Dexterity and stimulation of sensory receptors strengthen those afferent and efferent neuromuscular pathways. Hand Task Training—understanding what is in your hands and being able to sense what is in their palms and fingers and with graded difficulty can move on to more specific tasks. Optimizing those sensory pathways will assist with progressing the patient towards those specific tasks towards restoring quality of life though the activities of daily living.

Physical Therapy include Lower Extremity and functional movements—Dexterity and stimulation of sensory receptors strengthen those afferent and efferent neuromuscular pathways. Gait Training—understanding what is under your feet and being able to sense what is under ones feet and toes will improve the foot-floor pathways and adaptation to those surfaces. Best way to train is to go from non-weight bearing to weight bearing activities either within the Open Chained or Closed Chained Training Methodology. This is a way to grade difficulty but also limit fall risks for those who are at a fall risk but still train toe and foot plantar sensitivity. Toe and Foot Flexion and Extension. But most importantly rotational component associated with the foot-ankle and knee movements. Stroke Patients, and amputees (stimulation of the corresponding limb will increase trainability in addition to the future use of a prosthetic limb, Muscular Dystrophy, Elderly Population, Lower Extremity Replacements, (Hip, Knee, Foot-Ankle), Newly Injured Population.

The invention is sport specific. As one becomes more in-tune with their playing surfaces and trains their feet and hands to be more aware of what they feel—it will create more muscle memory for the intrinsic and extrinsic of the foot and hand musculature. Training has positive impacts of balance and other postural movements. Reconnecting the mind back to the body and being able to track improvements throughout the training process will be key in proving this concept. Since this is a training method that can be done with or without weight bearing application, the use within bed-written hospital patients would be a wonderful application. There are many times that there is edema in the lower limbs and risk of blood clots due to the inactivity. Being able to stimulate and then train patients to move their lower extremities—foot ankle will initiate the body's own muscle pump system then progressing the fluid towards re-circulation.

Figure 7:
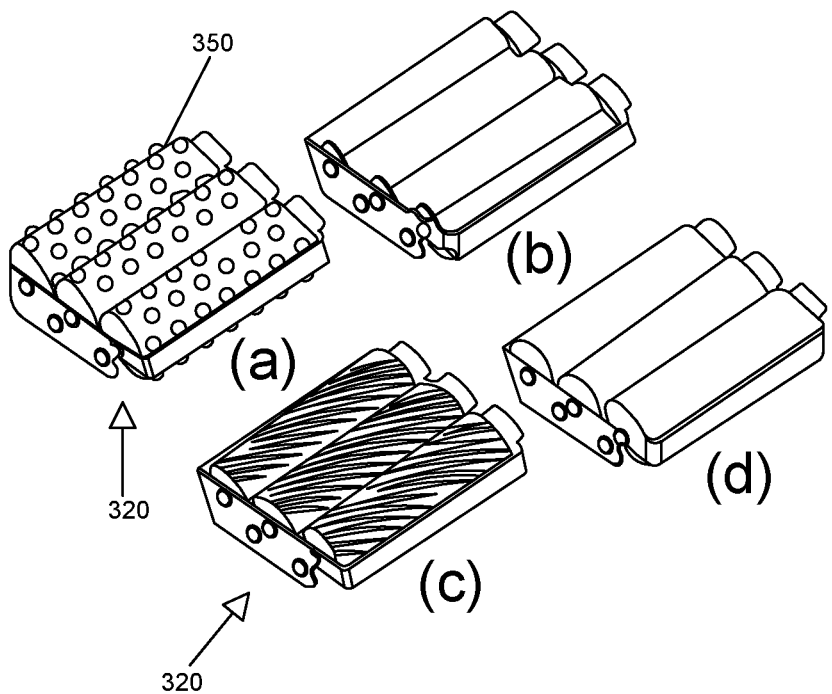
FIG. 7 shows alternative embodiments for the surface of the rollers.

FIG. 7 shows various alternative designs for the rollers 350. In FIG. 7A, the rollers 350 can have bumps dispersed over the entire surface of the rollers 350. In FIG. 7B, the bumps can be much smaller in size and greater and number. In FIG. 7C, the rollers can have an angled linear pattern. And in FIG. 7D, the surface can be flat. The surfaces can be of a rubber or elastic, though in FIG. 7D the surface is sticky. While it is shown that each of the rollers 350 in a particular roller cassette 320 are all the same, it should be appreciated that the rollers 350 can be interchanged such that the rollers in a cassette 320 have different surfaces. A user can then exercise using the different roller cassettes 320 to re-stimulate or provide different stimulation to the foot (or hand).

Figures 8A, 8B:
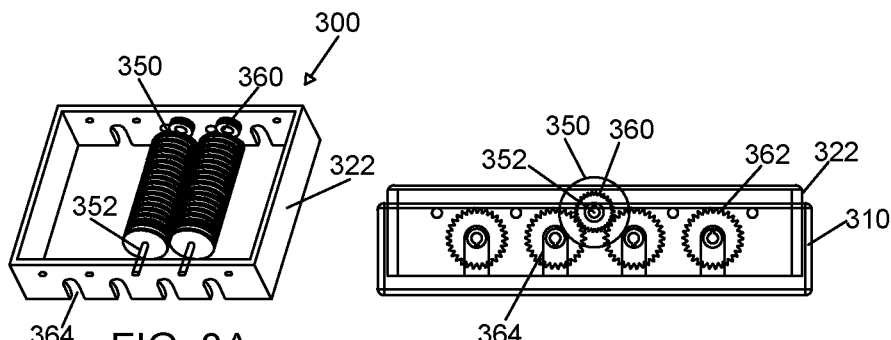
FIGS. 8A-I show various alternative embodiments for the roller cassette.

Turning to FIGS. 8A-G, further illustrate one detailed embodiment of the roller system 300 is shown. In FIG. 8A, the roller cassette frame 322 is shown. As noted above, each roller 350 is attached to two opposing sides of the frame 322 by a pin 352 that extends through the center of the roller 350. A drive gear 360 is provided at one end of the pin 352. As shown, the drive gear 360 is attached to the pin 352 by a threaded screw fastening device, so that the drive gear 360 rotates with the pin 352 as the user rotates the roller 350. However, the drive gear 360 can also be attached to the pin 352 by other means, such as an adhesive, solder, or the like.

In FIG. 8B, the drive gear 360 is shown as part of an overall drive chain. The drive chain includes the drive gears 360 of the rollers 350 interconnected to one another through a series of driven gears 362. The driven gears 362 are rotatably attached to the roller cassette frame 322, such as by being located in an inverted U-shaped slot 364 in the frame 322. The driven gears 362 can be rotatably fixed to the housing 310. Accordingly, the driven gears 362 extend from the housing 310 into the frame 322 through the slot 364. As the frame 322 is lowered into the housing 310, the driven gears 362 enter the slots 364. The drive gears 360 and driven gears 362 are positioned so that the teeth of the drive gears 360 cooperatively engage the teeth of the driven gears 362. The drive chain interconnects all the rollers 350 together, so that all the rollers 350 rotate in unison with one another. Thus, when the user rotates a first roller 350, the remaining rollers 350 also rotate. Of course, one or more of the rollers 350 need not be interconnected, on that it can rotate independent of the other rollers 350.

Figures 8C, 8D:
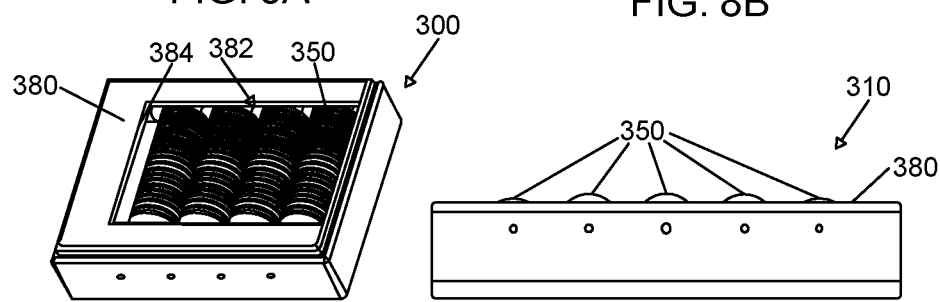

Referring to FIG. 8C, the roller system 300 can also include a top cover 380. The top cover 380 fits over the top opening of the housing 310. After the cassette 320 is placed in the housing 310, the cover 380 is placed over the housing 310 to enclose the cassette 320. The cover 380 can either engage the housing 310 or the cassette frame 322. The cover 380 has an opening 382 that is aligned with the rollers 350. As shown in FIGS. 8C, 8D, the rollers 350 come through the opening 382 and extend slightly outside and above the housing 310 and the top cover 380. In this way, the user contacts the rollers 350 and the top cover 380 prevents the user from being injured or coming into contact with the inside of the housing 310. The inner circumferential edges 384 of the opening 382 are curved or angled to further prevent injury of the user during use.

Figures 8E, 8F:
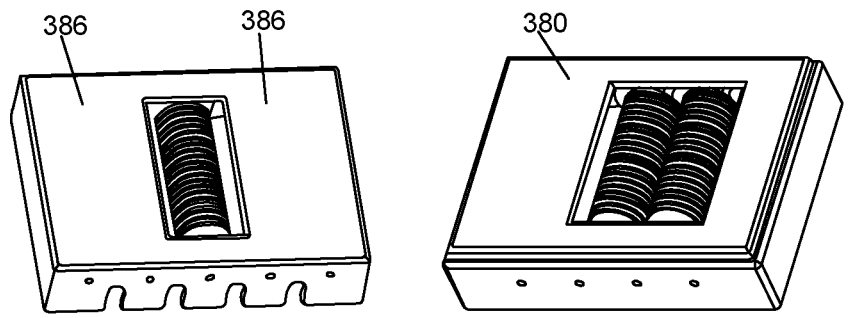

As shown in FIG. 8E, the roller system 300 can be configured to provide a single roller 350. Or, the opening 382 of the top cover 380 can be configured to only allow one of multiple rollers 350 to be used. In the present embodiment, the opening 382 is located at about the center of the cover 380 and is surrounded by two side surfaces 386. The side surfaces 386 of the cover 380 are smooth and provide a different stimulation to the foot of the user during use. As shown in FIGS. 8E, 8F, the rollers 350 can be positioned to one side and one of the side surfaces 386 can be larger than the other. Still further, the cover 380 can have multiple openings 382 separated by an intermediary surface of the cover. Or, as shown in FIG. 8I, the opening 382 can expose only a portion of one or more rollers so that the cover 380 covers over a portion of the roller. For instance, the opening 382 can have a pentagon shape that only exposes part of five rollers. The shapes of the covers can be but are not limited to triangles, squares, rectangles, circles, ovals, diamonds, pentagons, hexagons, septagons, octagons, decagons, etc.

Figures 8G, 8H:
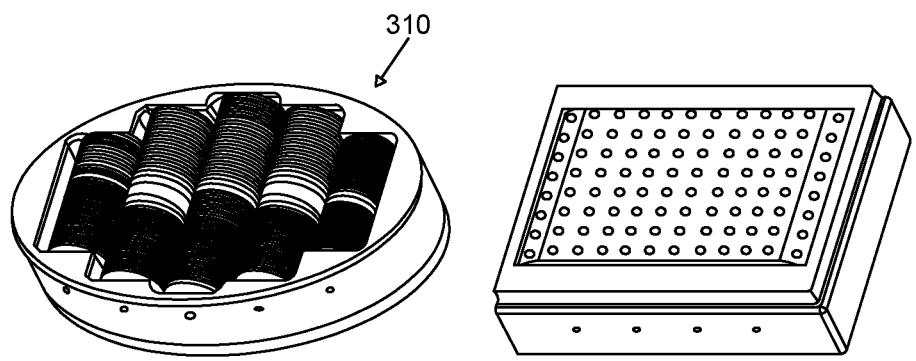
Figure 8I:
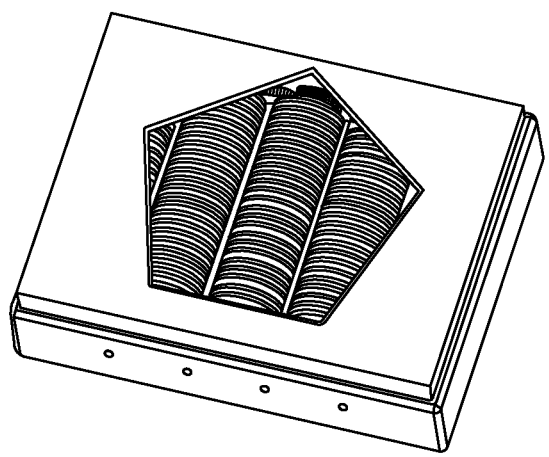
Figure 10A:
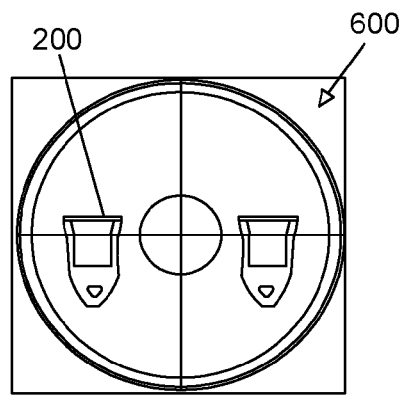
FIGS. 10A-E show a rotating disc in accordance with an alternative embodiment of the invention, where
Figure 10B:
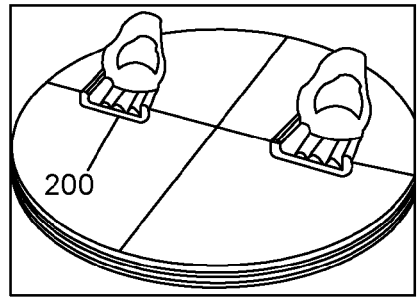
Figure 10C:
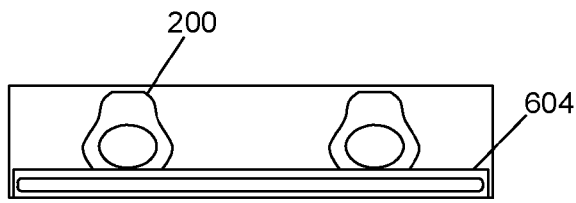
Figure 10D:
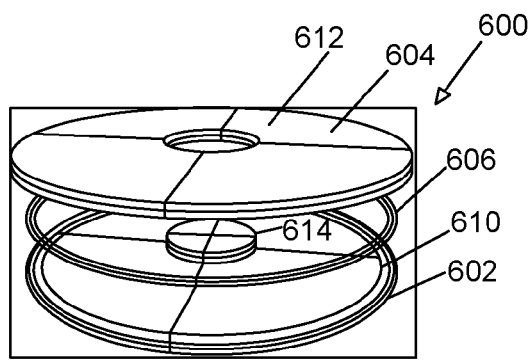
Figure 10E:
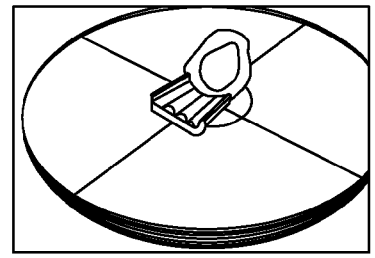

As further illustrated in FIG. 8G, the roller system 300 can have an oval shape with larger and smaller rollers 350. As shown in FIG. 8H, a conveyor belt can also be provided. Here, the conveyor belt is fastened around two or more rollers so that the belt rotates around the rollers. This provides a more uniform surface. A stimulation material, such as SPNRED, can be attached to the outer surface of the conveyor belt.

Another embodiment of the roller cassette 390 that can be used in the housing 310 of the roller system 300 is shown in FIGS. 9A-C. As best shown in FIG. 9B, the cassette 390 is formed by a single large roller 392 and a frame 394. The roller 392 is rotatably connected to the frame 394 in any suitable manner, such as by a pin 352 that extends through the roller 392 and engages openings in opposite sides of the frame 394. Referring to FIG. 9A, the roller 392 is located in the center of the cassette 390, and the frame 394 includes two angled ramp portions 396 on either side of the roller 392. The ramp portions 396 are angled up toward the roller 392, which extends up above the ramps 396. Accordingly, the ramps help guide the user's toes toward the rollers, and provide a different stimulation surface for the user.

Figure 14A:
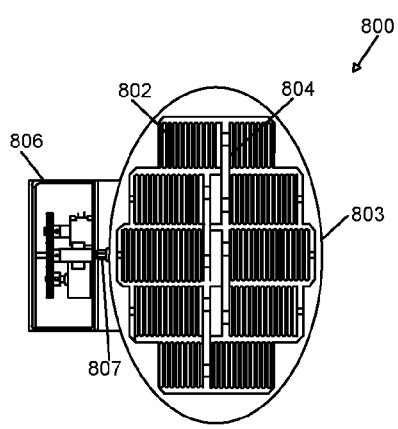
FIGS. 14A-D show an alternative embodiment of the roller system 300 in accordance with the invention.
Figure 14C:
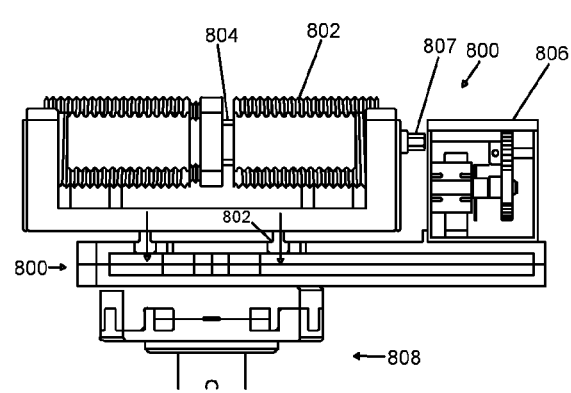
Figure 14B:
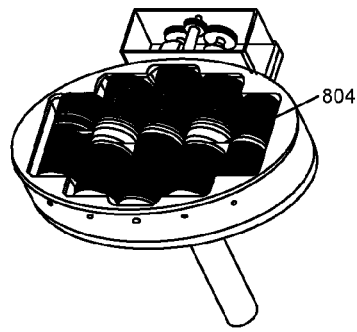

Another alternative embodiment of the exercise system 300 of FIG. 1 is shown in FIGS. 14A-B. Here, an exercise system 800 is provided that also has rollers 802. The rollers are arranged in an oval-shaped housing 803, though any suitable shape can be provided. There are 8 rollers 802 in the embodiment shown. The rollers 802 are connected together by one of two belts 804. Accordingly, the top roller 802 and the three rollers on the right (in the embodiment) are connected by a first belt 804. And the bottom roller 802 and the three rollers on the left are connected together by a second belt 804. A motor 806 is provided in a motor housing that is separate from the roller housing 803. The motor 806 is connected to the belt by a rotation chain that includes one or more axles 807 and may also include various gears and the like. The motor 806 turns the rotation chain to rotate the axle 807, which in turn rotates the belts 804. The rotation chain can be configured so that the two belts 804 rotate in the same direction, or in different directions. The motor can be used to assist or add an element of resistance to the exercise to either make it easier or harder for the user.

In FIG. 14C, the assembly of the exercise system 800 is shown in greater detail. The system 800 includes the roller housing 803, base 801, and motor assembly 806. The housing 803 is a separate element that has one or more (and preferably at least two) locking tabs 802 that project downward from the bottom surface of the housing 803. The locking tabs 802 removably engage openings in the top surface of the base 801. In the embodiment shown, the tabs 802 have a neck and an expanded head. The tabs 802 enter a wide part of the opening (as shown in FIG. 14C). At that point, the housing 803 is pushed to the right (in the embodiment), so that the axle 807 is received by and engages a mating fastener opening in the motor 806. At the same time, the tabs 802 enter a narrowed portion of the base openings, thereby locking the tabs 802 in the base openings so that the housing 803 cannot be pulled directly up. To remove the housing 803, the user must push the housing 803 to the left (in the embodiment) and then lift the housing 803 from the base plate 801.

Figure 14D:
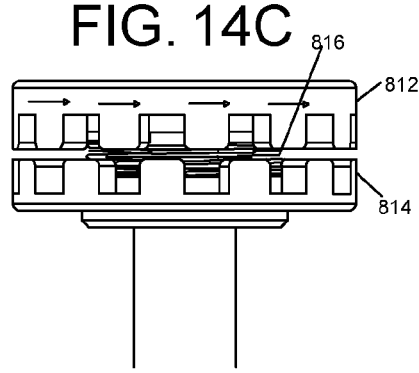

A support 808 is shown connected to the bottom of the base plate 801. As best shown in FIG. 14D, the support 808 is an elongated member with a large head 810. The head 810 includes a top plate 812 and a bottom plate 814. The plates have teeth that mate with each other. An inwardly biased spring 816 is provided between the plates 812, 814 to keep the plates 812, 814 together. The user can pull the plates 812, 814 apart against the force of the spring 816, rotate the plates 812, 814 with respect to each other, and then allow the plates 812, 814 to come together. In this manner, the user can adjust the direction that the housing 803 and the rollers 802 (see FIGS. 14A, B) face with respect to the user's foot. The teeth allow the housing 803 to be rotated at small increments (for example, 5° at a time) so that the housing 803 can face any desired direction.

Turning to FIG. 10A-D, the foot receptacle 200 of FIGS. 1-4 can also be attached to a large rotational device 600. The rotational device 600 is circular and flat and includes a base plate 602 and a rotating disk or top plate 604. The base plate 602 has a central post 614 that projects upward from the base plate 602. The top plate 604 has a central opening 612 that receives the post 614 of the base plate 602. The ball bearings 606 form a chain that rests in a channel 610 at the outer circumferential edge of the base plate 602 and a corresponding channel at the outer circumferential edge of the top plate 604. The post 614, ball bearings 606, and opening 612 cooperate to allow the top plate 604 to swivel or rotate about the base plate 602. The rotating disk 604 is rotatably connected to the base plate 602, such as by ball bearings 606 or the like. In addition, a sensory material (such as SPNRED) can be provided on the top surface of the top plate 604.

The locking tabs 208 of the foot receptacle 200 can lockably connect with mating openings in the top surface of the rotating disk 604, or other suitable locking mechanisms can be provided. Two foot receptacles 200 can be coupled to the rotational device 600. The mating openings are configured so that the foot receptacles 200 are aligned and separated from one another at about a diameter of the device 600, so that the user can balance on the device 600. The user can then perform additional exercises using the rotational device 600. The rotational device 600 can also be integrated with a frame similar to the one shown in FIG. 5. Since the foot receptacle 200 includes proprioceptive material 210, the user would have the benefit of that stimulation. In accordance with an alternative embodiment, a single foot receptacle 200 can be positioned at the top of the center post 614. In this manner, the user can use his/her toes and foot to rotate the top plate 604.

Thus, the exercise device of FIGS. 1-10 and 14 can be used for a single foot (FIGS. 1-4) or both feet (FIG. 5) while the user is sitting or standing. In use, the user needs to rotate his/her entire foot in order to pass his/her toes over the rollers 350. As the user grabs or flicks the material (which is secured to the rolling pin like structure including but not limited to adhesives, Velcro, and sewing) it rotates towards and away respectively in relationship to the user. This rotation and revolutions of the material triggers a tracking and counting device including but not limited to a combinations of sensors that are embedded within the edges of the proprioceptive material and the physical housing of the structure, sensors using magnetic, light sources, temperature principals. This counting and tracking device will track all but not limited to speed/velocity, revolutions/repetitions, force, pressure, magnitude, and time of the bout of exercises.

The concentric activity is when the user flexes the toes and associated muscles of the foot. Within this activity there is light eccentric loading occurring during the phase where the user returns the toes back to a neutral position while letting go of the material. If the user would like to work on toe extension, then the user would extend and flick the material away causing the rolling pin structure to anti rotate but still causing a sensor to capture data on the metrics provided above. The flicking movement is the concentric activity, minimal eccentric loading occurs during this activity. Thus making way to the toe tube strengthening, which is discussed in further detail below.

Closed chained exercises are when the foot is weighted on the device which is placed on the planar surface. The closed chain exercises are limited to rotational based exercises, including foot and Ankle Supination and Inversion. As the user is properly set up in the device this exercise can be done sitting and/or standing. For example, using the right foot, the foot starts in a neutral position where the foot drags puts pressure on the material thought the metatarsal heads on toes. Utilizing the invertors and tibialis anterior, the user is able to swipe the material from Right to Left aka (medially move the foot and ankle) to then successfully move the material. Then like a type writer the foot will evert laterally then proceed to grab the material and supinate/invert medially to thus move the material medially. This strengthens the toe flexors, foot supinators and invertors.

This also includes Foot and Ankle Pronation and Eversion. As the user is properly set up in the device this exercise can be done sitting and/or standing. For example the right foot. The foot will start in a neutral position where the foot puts pressure on the material thought the metatarsal heads on toes. Utilizing the evertors (Peroneals) and Tibilais Anterior, the user is able to swipe and flick the material from Left to right aka (laterally move the foot and ankle) to then successfully move the material. Then like a type writer the foot will supinate medially then proceed to grab the material and evert/pronate laterally to thus move the material laterally. This strengthens the toe flexors and extensors, foot pronators and evertors.

FIGS. 11A-E illustrate another embodiment of the invention. Here, a flexibility strap 650 is connected to a foot plate 652. A connector is attached to the ends of the flexibility strap 650. The flexibility strap extends through two slots in the foot plate 652 and the connectors engage the foot plate 652 on the opposite side. A user's leg is shown in the foot plate 652. The user pulls on the flexibility strap 650 to add a level of resistance to a range of exercises. In addition, although a foot plate 652 is shown, the foot receptacle 200 of FIG. 1 can be utilized with other exercise devices such as with the flexibility strap 650. For instance, the foot receptacle 200 can be attached to a flexibility strap 650 to perform other exercises. The flexibility strap 650 can be attached to the strap 204 or buckles on the strap 204, and the flexibility strap can be used to stretch or exercise the leg muscles.

The invention utilizes two straps that are attached to a base where the material can be but not limited to a woven poly laminate webbing, medical grade foams, spandex, with an outer material of an aramid fiber weave. The aramid fiber weave is used for its high tensile strengthen and a force transmission throughout the material. Therefore, light assistance from the action of pulling the straps towards or away from the person will equate directly to the stretch. The user does not have to yank on the straps to feel the stretch or assist. The material that is in direct contact with the users foot is a SPNRED Material that will assist with the stimulation of the plantar surface and the other parts of the material that connect to the user. The two straps then coalesced into one strap. The primary two straps have an area of Velcro, tie, secure in a different way than explained to then attach them to create one strap.

When performing Lateral and Medial gastric belly head stretches, it is key to have multiple straps for proper assisting within Active Isolated Stretching technique. When activation of the muscles in the direction instructed, effectively using the strap that is in that direction defends from slippage of material from against the foot in addition to a more effective assist. The design is aimed at stretching angular movements throughout the lower extremity. The pinnate structure of the muscle enables the user to stretch in an infinite amount of directions. The wide base of the foot hold and the increased surface area of the lower material enable the user to be more strategic with the angles want to the stretch the calf and or any lower extremity stretch.

When performing Distal Hamstring stretch with the proper assist, there are three primary directions needed to perform the stretch effectively. Kicking the leg straight away utilizes the two final straps to be attached into one. When performing the stretch for the medial hamstring muscle belly, the user must take both straps and wrap them around the inside part of the leg to point the toes inward and also maintain an internal rotation set up for the lower leg. To stretch the lateral hamstring muscle belly, the opposite must occur—therefore both straps will wrap around the outside of the leg to maintain toes pointed outward and the leg externally rotated. The use of the two straps greatly enhances the degree of assisted rotation of the limb to isolate the targeted muscle. On and around the straps is enveloped in SPNRED material to increase stimulation of the hands and palmar surfaces during the stretching function the hands will be equally stimulated.

The flexibility strap 650 travels the posterior of the leg with a gap of space left for the user's calf. Buckles on this material allow for the user to customize the length of the straps to allow for larger or smaller users to use the same strap size. Straps can be tightened or loosened.

A Velcro strap 5 for above the knee to limit slipping downwards during use with the stretching strap. The material wrapping around the leg is lined with the SPNRED material to improve stimulation of the skin receptors. The strap that crosses atop the knee strap will have three protruding pieces of material such as but not limited to rubber, plastic, foam, silicone, organic and inorganic material. These three protrusions are adjustable to then correspond and line up with some landmarks on the knee (as illustrated by elements labeled 1, 2, 3 in FIG. 11C). These protrusions correspond to the superior lateral epichondyle to correspond with Vastus Lateralis, the superior to the patella (knee cap) to correspond with Rectus Femoris, and the superior medial epichondyle on the femur to correspond with Vastus Medialis. When working the quadriceps to stretch the hamstrings, the rubbing and stimulation of that area superior to the knee cap in those areas will assist in the distal activation of the Quadriceps and the consequent relaxation of the distal hamstrings, the key muscle were trying to relax and stretch. This action is key in reminding the user what muscles to use and where they will feel the body working. Utilizing the protrusions to the intended use will enable the user to physically touch and sensory activation of the muscle will assist in the physical activation of the said muscles.

Referring to FIG. 11D, a Velcro strap 6 is provided for around the dorsal arch of the foot to limit slipping upward during use with the stretching strap. The material wrapping around the foot will be lined with the somatosensory proprioceptive material to improve stimulation of the skin receptors. When working the Anterior Tibialis to stretch the calf, the rubbing and stimulation of the dorsal arch area in addition to two bulbous protrusions A1, A2, respectively, similar to what was described above will enhance the self stimulation of the particular area interested in working. The first protrusion A1 is place on the medial aspect of the foot targeting the Anterior Tibialis. The second protrusion A2 is attached to the lateral side of the foot targeting the Extensors Digitorum Longus will be key in reminding the user what muscles to use and where they will feel the body working. The key is to re-connect the users mind and body.

Figure 12:
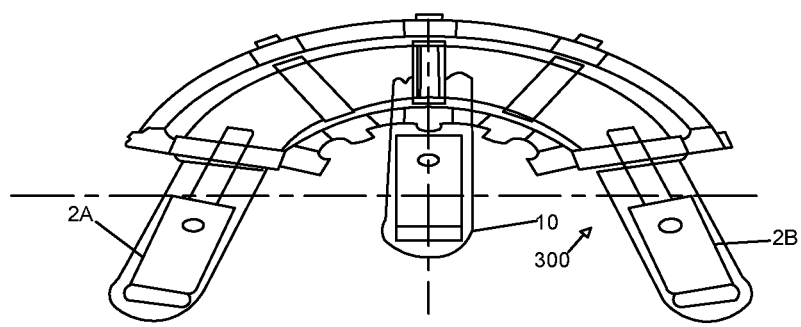
FIG. 12 shows another alternative embodiment of the invention.

Turning to FIG. 12, another illustrative embodiment is shown. Here, the exercise system 300 is formed with an ellipse shape that allows for a more ergonomically and biomechanically correct motion when performing Inversion, Eversion, Supination, and Pronation. The device includes a frame that supports rollers (five rollers are shown, though any suitable number can be provided). An SPNRED material is layered over the rollers and can rotate over the rollers, like a conveyer belt type operation (FIG. 8H).

The exercise device 10 can have a connection bar that can be attached to a receiving connector on the exercise system 300 at a number of positions. Exemplary foot positions 1, 2A, 2B are shown, including the foot positioned 2A, 2B at the ends of the device, or positioned 1 at the middle of the device. The user can rest his/her foot on a pedestal or the like, which is shown beneath the respective foot positions 1, 2A, 2B. The pedestal has a connecting bar that extends out from the pedestal that is slidably received in respective openings of the frame at each of the positions 1, 2A, 2B to put the pedestal at each of the three positions 1, 2A, 2B shown. Foot position 1 allows the user to perform inversion, eversion, supination and pronation. Foot position 2A allows the user to perform toe flexion, extension, abduction, and adduction for the left foot comfortably so the user can transition from one exercise to the other very quickly. And, foot position 2B allows the user to perform toe flexion, extension, abduction, and adduction for the left foot comfortably so the user can transition from one exercise to the other very quickly.

With respect to Turf Personalization, Somatosensory Proprioceptive Neuromuscular Material can be but not limited to the materials discussed above. A sensor can be embedded within the material where as it rotates, and the sensor transmits its detected data to the data capturing device. The sensor can be enclosed in a protective layering where sweat, dust, and other debris will not negatively affect data capturing and communication. The material can be removed via Velcro and cleaned with hot soap and water and hang dry. There are some organic cleaning solvents on the market that are used specifically for cleaning turf. The Personalization anywhere on the material can be applied using the information discussed above in prior information.

As shown in FIG. 12, foldable hinges on the feet of the base of the device. The base has foldable legs for hinges to improve the towage and portability of the exercise device. The center piece has a sausage joint that allows for complete folding capabilities of the device. Resistance can be added to the exercise, such as Magnetic Resistance, stretching the material so there is more friction, bands, tightening the rolling pin units. The Total Width is 15 inches. The Material Track is 4.5 inches wide, and folds up in to 7.5 inch×4.5 inch.

Figure 13:
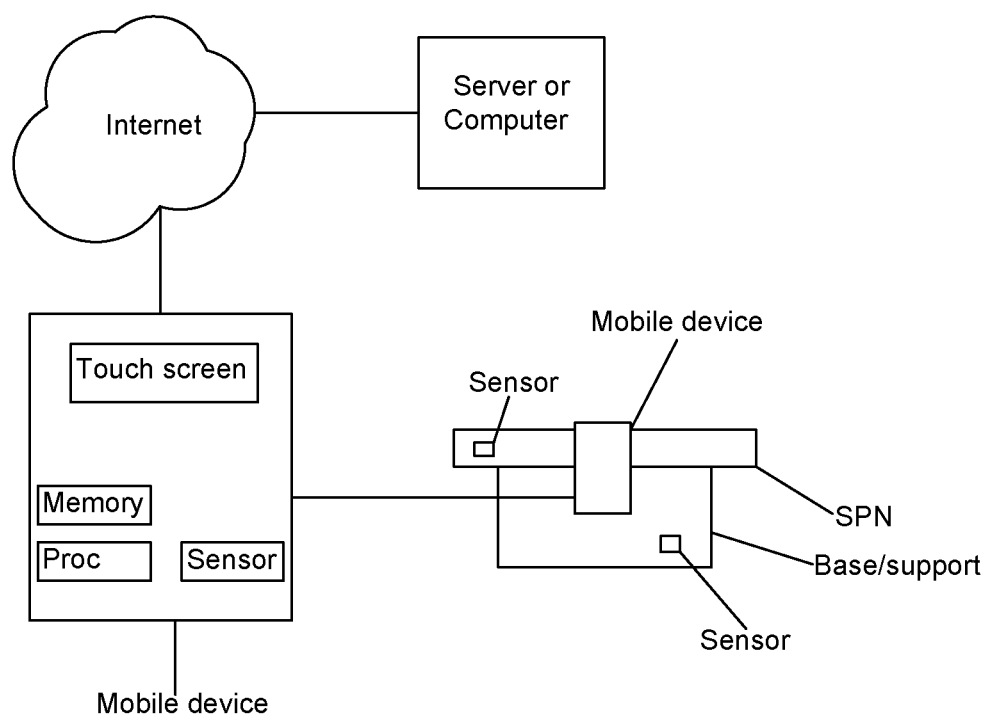
FIG. 13 shows the tracking and reporting system of the invention.

Turning to FIG. 13, the present invention also includes a data capturing device such as but not limited to being embedded within the system and structure itself, the use of an accelerometer, and or the use of the gyroscope within a user's mobile device. As noted above, the data capturing device can be a mobile smart phone that is attached to one of the arms, such as the tracking device 410 of FIG. 1. The data is Bluetooth, wirelessly, and or wired upload their data in real time to both the user and the practitioner's secure profile via a cloud based or server based format. The external electronic device associated with the exercise device (computer, tv, mobile phone, and or tablet) assists the user experience, having workouts (Strength and Flexibility), previous workout results in a timeline fashion, and a social media aspect to communicate a support network and even compete with friends, family, or teammates. Having the ability to track both the quantitative and qualitative data extracted from exercise bouts can assist within the accountability measures and compliance of an exercise program. The device and associated mobile application enables the user to track both quantitatively and qualitatively how they are feeling, what they enjoyed about the workout, plus other questions, in addition to the actual metrics of the workout to assist with the practitioners SOAP (Subjective-Objective-Action-Plan, which are notes that medical personnel write discussing patient interaction and evaluation) note creation and monitoring.

For example, a physician might like to maintain correspondence with a patient pre- and post-surgical intervention and throughout the rehabilitation process. To have some accountability measures for the patient, the physician could prescribe this exercise device as a means to track their quantitative data and tailor their exercise program wirelessly in person. The patients data would be secured based on HIPAA compliance and be encrypted and monitored to ensure safety and may also anonymize identification information. The physician will be able to create more in-depth SOAP (subjective, objective, action, plan) notes and closely monitor their patients programming either remotely or by satellite.

The present invention revolutionizes the way people exercise under a medical professional's care. It reduces costs of having to directly monitor a patient's workouts once they have progressed from their standardized rehabilitation care to performing the exercises at home or during travel. It improves compliance and thereby reduces the amount of time it takes for them to get better.

As shown in FIG. 13, the mobile device can have a processor with a memory and an input device such as a keyboard or touch screen. The processor operates software that permits the accessing of data from an electronic information source. The information may be stored on the mobile device, hard drive, memory stick, or on any other appropriate data storage device. It can also be in wired or wireless communication with a remote processor such as a computer with a memory, input device, and accesses a local or global network such as the Internet to communicate with a remote server or computer such as via a website.

As further shown in FIG. 13, the exercise device can have a sensor located on the base and/or arm, and/or one embedded in the SPNRED material. A sensor can also be located inside the mobile phone. The sensors can be suitable to detect various things, such as motion, noise, pressure, and the like, that can be processed by the processor at the mobile phone or a processor on a remove server or computer to track the user exercise activity. Accordingly, the sensors can be, for instance, 360° potentiometers, triaxial sensors, gyroscopes, and/or accelerometers. Other suitable sensors include an EMG (that checks the electrical stimulation generated by the muscle), internal measurement unit (IMU) (e.g., in the foot receptacle to determine range of motion). In one embodiment of the invention, a pressure sensor can be provided at the platform 206 of the foot receptacle 200. Any suitable pressure sensor can be utilized, such as a pressure plate, plantar pressure meter, or center of pressure (COP) or center of pressure/sway meter. The pressure plate can be used to determine the balance of the user.

An application could be a mobile application, including an application that can run on devices such as iPhones, androids, iPads, android tablets, computers, and/or smart TVs. The application could run on any other suitable electronic device. The device has a proprietary application directly associated with the tracking, communicating, and data storage of the user's personal, health, and exercise information. Information can optionally be encrypted and monitored to ensure safety. The application serves as a tool to create accountability and improve compliance associated with home exercise programming. The application can use a mapping system to underlay the routes in association with the GPS function of the phone to track mileage, running speed, split times, etc. There is a social media component associated with the tracking device of their exercise output and sharing that information with friends via Facebook, Twitter, and other social media sites and proprietary owned site.

The data collected and updated based on answering questions that are qualitative in nature are aimed at providing a safe environment for interpersonal competition and intrapersonal competition. Gaining positive reinforcement for performing your exercises will enhance the compliant mindset that the present invention is trying to provide. The data collected will serve as either qualitative or both qualitative and quantitative. Once logged into the mobile application, the device and the mobile application will prompt the user to sync the device and the mobile device to update the user's status and progress. Different pictures of smiley faces could correspond to a number for both quantitative and qualitative measurements. The application could ask the user how he or she is feeling, with the response recorded by selecting the appropriate smiley face, visual analog scale (VAS) (see FIG. 16H, 936, 938).

This application provides the GPS function and social media sharing function for those who are not currently involved in patient care to keep within HIPAA compliance and laws. If users are using the device for self-prescribed injury rehabilitation, injury prevention, and/or sports performance then they are able to share their data with friends and/or a social network. Users can also share their data. All information is given with consent and user agreements signed to show acknowledgement of the terms and service associated with the product and the associated mobile application.

If no mobile application is applied, a DVD or CD can be uploaded to the user's computer, smart TV, and other electronic devices. HDMI Output can be provided so that the exercise device can be hooked up to the TV to gain real time metrics and data during exercising. The DVD provided has the proper stretching and strengthening routines for the user to follow.

Data for Patients and Doctors include data capturing systems. Utilizing sensors embedded within the proprioceptive material, within the housing of the structure, within the resistance methods (bands, tubes, cables, weights), Internal and External Accelerometers, GPS Devices, gyroscope of a phone, or an external system that is capable of tracking those metrics, the device can communicate data through the use of Wireless/Bluetooth/radio signaling/Wired Upload of data in real time and sent to a medical professional. The device can be HIPPA compliant, so that doctors can have the ability to tailor rehabilitation program wirelessly and provide updates by mobile device, tablet, laptop, phone, and personal computer.

Figure 15A:
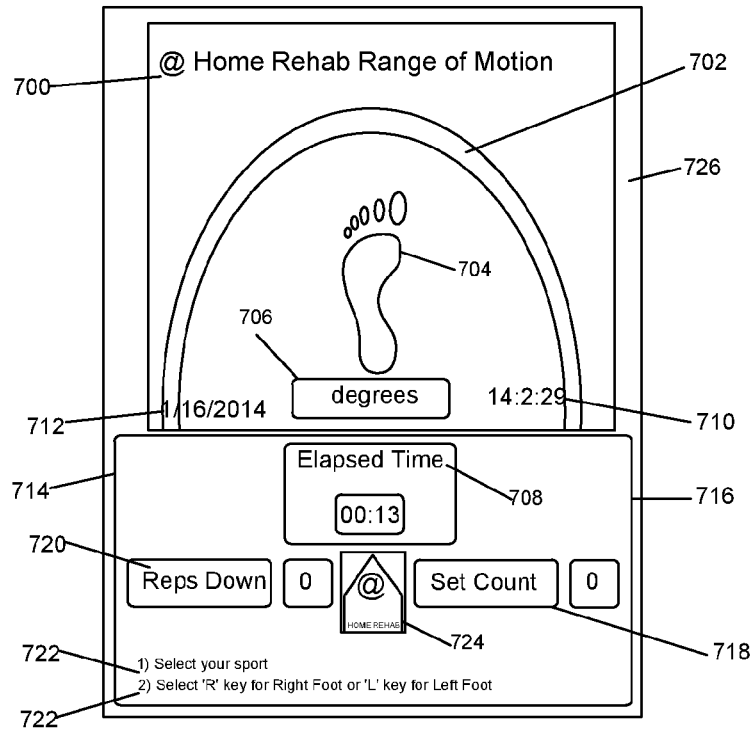
FIGS. 15A-K show the tracking system of the invention.

FIG. 15A represents the Range of Motion (ROM) program for the foot that can be selected from the desktop application home screen pictured. This exercise program includes the program title 700 and program instructions 722. The instructions 722 allow the user to identify the program they want to selected, and enables the user to select from interchangeable backgrounds which are identified by 726. The user can also choose the foot that they are rotating or any other anatomical area that would be trained. For logging purposes both the current date 712 and time 710 as well as the elapsed time taken to complete the exercise regimen 708 are presented to the user. As the user rotates their foot within the exercise device, the on screen foot 704 rotates to either the right or left with both indicators in degrees of rotation 706 and on screen mock light emitting diodes (LEDs) 702 providing visual feedback to the user. A rep counter 720 and set counter 718 are included with 702 and 706 to provide a comprehensive form of data collection within the program. Counting of both of these parameters is represented by additional on screen LEDs 714 and 716 to provide additional forms of visualization for the user. These LEDs range from red to yellow to green, and light up according to how far the foot is rotated. The green LEDs serve to let the user know when the optimum range of motion has been reached by the user. The following program components 702, 704, 708, 710, and 712 are all automatically recorded and saved for tracking of user progress within each program that exists within the desktop application. This data is available for viewing by the user in the Results section of the application viewable in FIG. 15I. Different versions of this and additional programs with varying depictions of 726 can be viewed in the accompanying figures.

Figure 15B:
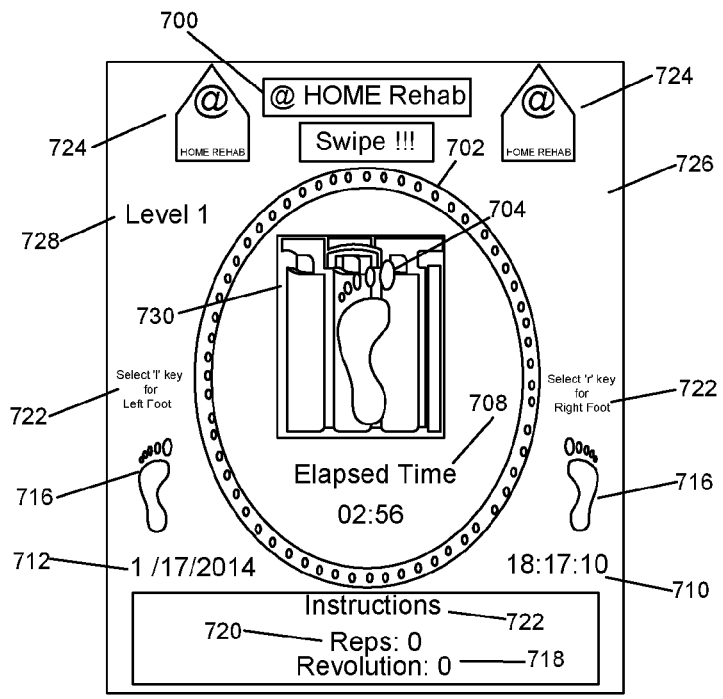
Figure 15C:
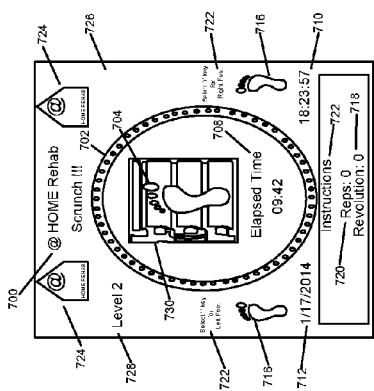
Figure 15D:
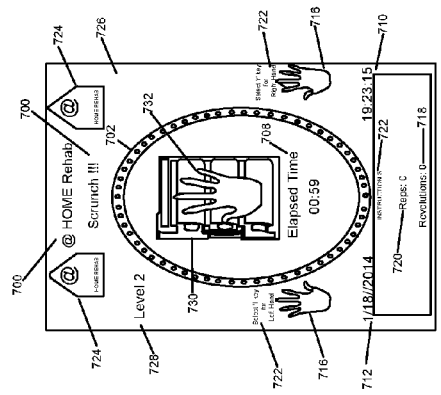
Figure 15E:
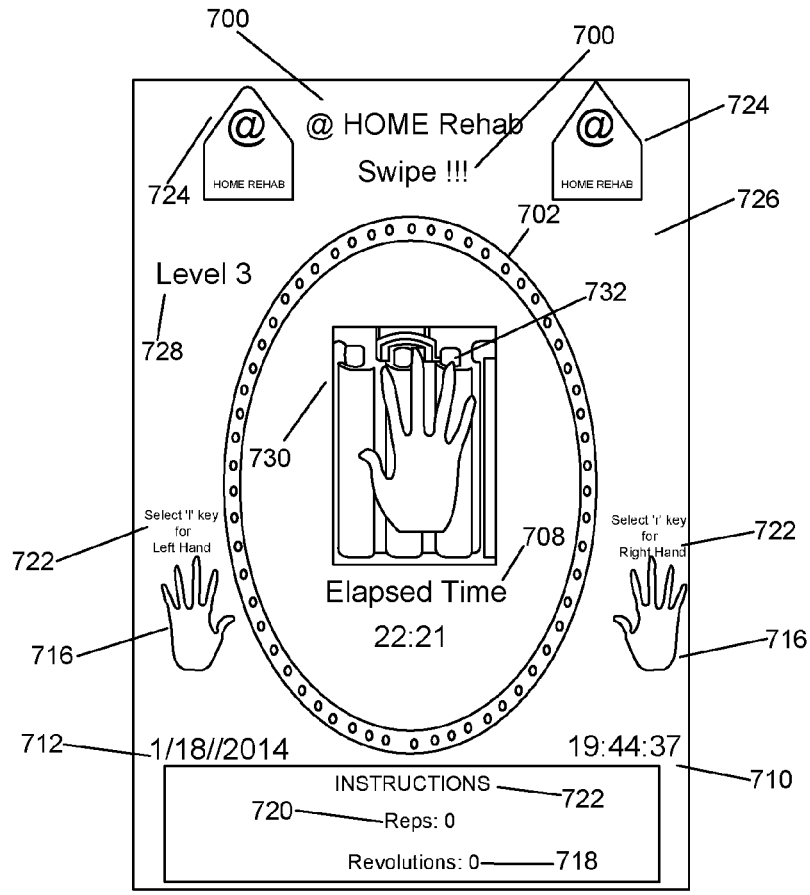
Figure 15F:
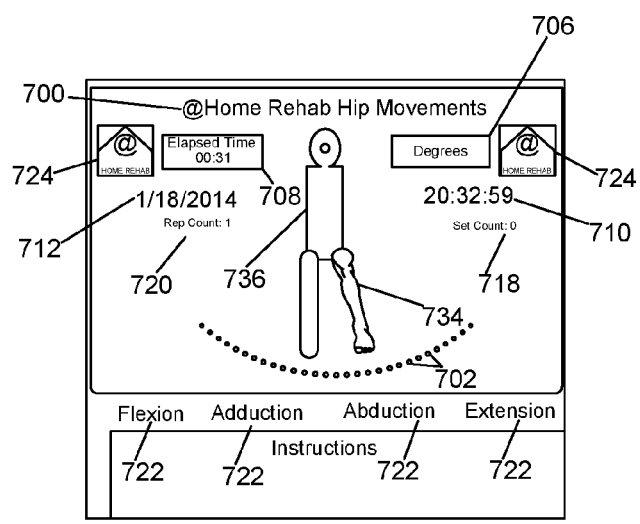
Figure 15G:
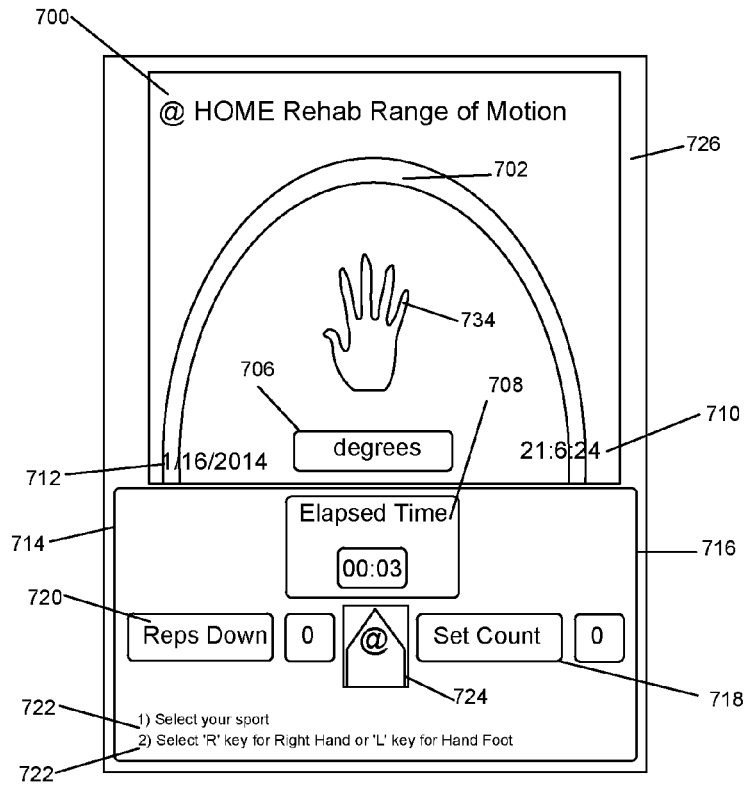
Figure 15H:
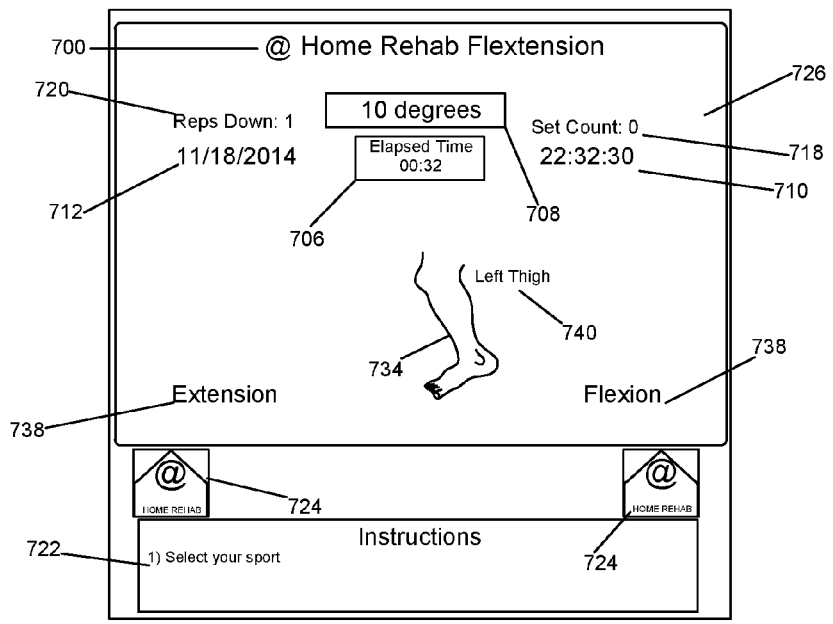
Figures 15I, 15J:
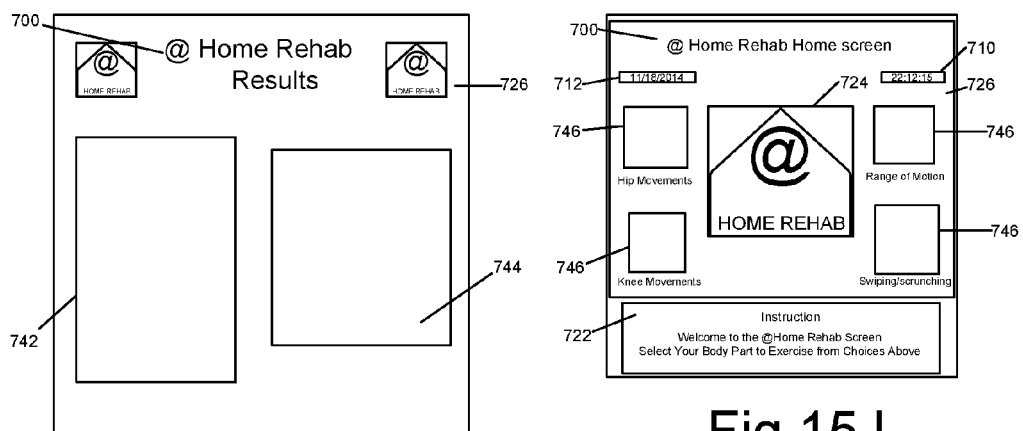

FIG. 15B represents the foot swiping program that can be selected from the desktop application home screen pictured in FIG. 15J. This program includes components 700-726 that are used for the same purpose as in FIG. 15A as well as additional components to necessary to enhance the user experience for the desired exercise. The exercise pictured in the above figure collects data when the user swipes their foot across the rollers of the exercise device. The on screen rollers 730 allow for visualization of this within the desktop application. This program allows for the user to select from varying levels of difficulty represented by 728, with the number of on screen LEDs 702 lighting up in different numerical increments. The three levels for user selection are Level 1 (easy), Level 2 (medium), and Level 3 (difficult). In Level 1, each time the user swipes their foot across the rollers a rep 720 is recorded and 15 green LEDs light up with 4 reps equaling one revolution 718 (or set) where all of the LEDs are lit up within the circle before they reset to indicate the beginning of another revolution. In Level 2, 10 yellow LEDs light up each time the user completes a rep with 6 reps equaling one revolution. In Level 3, 6 red LEDs light up each time a rep is completed with 10 reps equaling one revolution. This program is designed to be a timed program where the user attempts to complete as many reps and revolutions as possible during the pre-defined duration of the exercise. Each rep and revolution as well as the level of difficulty are automatically recorded and saved for viewing in the results portion of the program viewable in FIG. 15I.

FIG. 15C represents the foot scrunching program that can be selected from the desktop application home screen pictured in FIG. 15J. This program includes components 700-726 that are used for the same purpose as in FIG. 15A as well as additional components to necessary to enhance the user experience for the desired exercise. The exercise pictured in the above figure collects data when the user scrunches their toes along the rollers of the exercise device. The on screen rollers 730 allow for visualization of this within the desktop application. This program allows for the user to select from varying levels of difficulty represented by 728, with the number of on screen LEDs 702 lighting up in different numerical increments. The three levels for user selection are Level 1 (easy), Level 2 (medium), and Level 3 (difficult). In Level 1, each time the user scrunches their toes along the rollers a rep 720 is recorded and 15 green LEDs light up with 4 reps equaling one revolution 718 (or set) where all of the LEDs are lit up within the circle before they reset to indicate the beginning of another revolution. In Level 2, 10 yellow LEDs light up each time the user completes a rep with 6 reps equaling one revolution. In Level 3, 6 red LEDs light up each time a rep is completed with 10 reps equaling one revolution. This program is designed to be a timed program where the user attempts to complete as many reps and revolutions as possible during the pre-defined duration of the exercise. Each rep and revolution as well as the level of difficulty are automatically recorded and saved for viewing in the results portion of the program viewable in FIG. 15I.

FIG. 15D represents the hand scrunching program that can be selected from the desktop application home screen pictured in FIG. 15J. This program includes components 700-726 that are used for the same purpose as in FIG. 15A as well as additional components to necessary to enhance the user experience for the desired exercise. The exercise pictured in the above figure collects data when the user scrunches their fingers along the rollers of the exercise device. The on screen rollers 730 and hand 732 allow for visualization of this within the desktop application. This program allows for the user to select from varying levels of difficulty represented by 728, with the number of on screen LEDs 702 lighting up in different numerical increments. The three levels for user selection are Level 1 (easy), Level 2 (medium), and Level 3 (difficult). In Level 1, each time the user scrunches their lingers along the rollers a rep 720 is recorded and 15 green LEDs light up with 4 reps equaling one revolution 718 (or set) where all of the LEDs are lit up within the circle before they reset to indicate the beginning of another revolution. In Level 2, 10 yellow LEDs light up each time the user completes a rep with 6 reps equaling one revolution. In Level 3, 6 red LEDs light up each time a rep is completed with 10 reps equaling one revolution. This program is designed to be a timed program where the user attempts to complete as many reps and revolutions as possible during the pre-defined duration of the exercise. Each rep and revolution as well as the level of difficulty are automatically recorded and saved for viewing in the results portion of the program viewable in FIG. 15I.

FIG. 15E represents the hand swiping program that can be selected from the desktop application home screen pictured in FIG. 15J. This program includes components 700-726 that are used for the same purpose as in FIG. 15A as well as additional components to necessary to enhance the user experience for the desired exercise. The exercise pictured in the above figure collects data when the user swipes their hand across the rollers of the exercise device. The on screen rollers 730 and hand 732 allow for visualization of this within the desktop application. This program allows for the user to select from varying levels of difficulty represented by 728, with the number of on screen LEDs 702 lighting up in different numerical increments. The three levels for user selection are Level 1 (easy), Level 2 (medium), and Level 3 (difficult). In Level 1, each time the user swipes their hand across the rollers a rep 720 is recorded and 15 green LEDs light up with 4 reps equaling one revolution 718 (or set) where all of the LEDs are lit up within the circle before they reset to indicate the beginning of another revolution. In Level 2, 10 yellow LEDs light up each time the user completes a rep with 6 reps equaling one revolution. In Level 3, 6 red LEDs light up each time a rep is completed with 10 reps equaling one revolution. This program is designed to be a timed program where the user attempts to complete as many reps and revolutions as possible during the pre-defined duration of the exercise. Each rep and revolution as well as the level of difficulty are automatically recorded and saved for viewing in the results portion of the program viewable in FIG. 15I.

FIG. 15F represents the hip exercise program available for the selection by the user in the desktop application represented in FIG. 15J. This program contains the same program components 700-726 that are available in each exercise program within the application. The on screen person 736 is necessary to provide the user with a visual representation of the exercise that they are completing. Within this program, the exercise device is attached to the user's foot for free movement of the desired leg. The different exercises available for user completion within this program are represented by 722 and are hip flexion, hip extension, hip adduction and hip abduction. Each time the user completes a rep with the device attached to their leg, the on screen leg 734 moves in conjunction with tracking the degrees of movement 706 for their leg and the on screen LEDs providing a colored representation of the quality of the degrees of movement. Each rep and set that is completed within this program is recorded and logged for viewing within the results portion of the desktop application viewable in FIG. 15I.

FIG. 15G represents the Range of Motion program for the hand that can be selected from the desktop application home screen pictured in FIG. 15J. This exercise program includes the program title 700 and program instructions 722 that allow for the user to identify the program they have selected, select from interchangeable backgrounds 726, and choose the hand that they are rotating. For logging purposes both the current date 712 and time 710 as well as the elapsed time taken to complete the exercise regimen 708 are presented to the user. As the user rotates their hand within the exercise device, the on screen foot 704 rotates to either the right or left with both indicators in degrees of rotation 706 and on screen mock light emitting diodes (LEDs) 702 providing visual feedback to the user. A rep counter 720 and set counter 718 are included with 702 and 706 to provide a comprehensive form of data collection within the program. Counting of both of these parameters is represented by additional on screen LEDs 714 and 716 to provide additional forms of visualization for the user. These LEDs range from red to yellow to green, and light up according to how far the hand is rotated. The green LEDs serve to let the user know when the optimum range of motion has been reached by the user. The following program components 702, 704, 708, 710, nd 712 are all automatically recorded and saved for tracking of user progress within each program that exists within the desktop application. This data is available for viewing by the user in the Results section of the application viewable in FIG. 15I. Different versions of this and additional programs with varying depictions of 726 can be viewed in the accompanying figures.

FIG. 15H depicts the knee flexion and extension program available for selection from the desktop application home screen represented by FIG. 15J. Containing the similar program components 700-726 found in the other desktop programs, the specific one is designed to track the user's movement while they are flexing and extending their foot with a bent knee. Upon selecting the program, the user can select which foot they are exercising, their desired background 726 and which movement that they are going to be completing. Once they have selected their leg, an on screen leg 734 and thigh 740 appear to provide visualization of the movement that is being completed. This program and the exercise device track the rep count 720, set count 718 and degrees of movement that the user has for the selected exercise. These are all saved and recorded automatically by the program for viewing within the results section of the desktop application.

FIG. 15I represents the results section of the desktop application that can be accessed by both the user and their doctor. This section contains both a documented and graphical representation, 742 and 744, of the data that is gathered from each of the different programs within the desktop application. This section allows both users and their doctors to track their own progress within their physical therapy regiment. Doctors can use this section to provide feedback to their patients in regard to their exercises and also change their regiment if necessary.

FIG. 15J represents the home screen for the desktop application. This is the first screen that the user is directed to after they log in to the application from the screen in FIG. 5K. On screen buttons 746 allow for the user to click and navigate between the different exercises that can be completed with the exercise device. By selecting one of the buttons, the user will automatically be transferred to the program they have selected within the application. These different programs are viewable FIGS. 15A-H. Once the user has selected their desired program, instructions 722 appear at the bottom of the program to help the user correctly use the program.

Figure 15K:
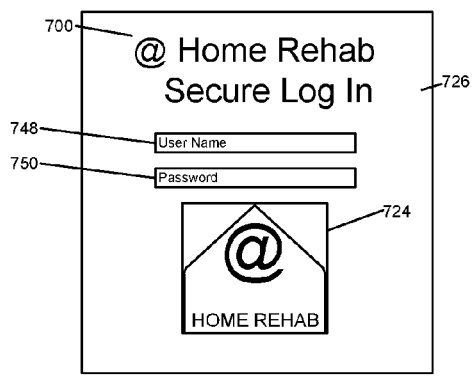

FIG. 15K represents the initial secure log in screen for the desktop application. Whether the log in is for a doctor or a patient each person that uses the exercise device and would also subscribe to have this software along with the device. Each user would have their own unique username 748 and password 750 in order to confirm their identity and ensure that no other user of doctor would have access to their account. Both the username and password could either be selected after subscription purchase or automatically assigned along with the subscription. The desktop application is one of two software interfaces, the other being a mobile application that this log in information would be used for. This application is made to allow patients the convenience of being able to complete their rehabilitation regiments at home while simultaneously uploading the data that is recorded and tracked for each exercise movement to a database that can be reviewed by both the patient themselves and their doctor. This also allows for a doctor to reach out to more patients at once and provide feedback to their patients based on the data that is uploaded from either the mobile or desktop application.

Figure 16A:
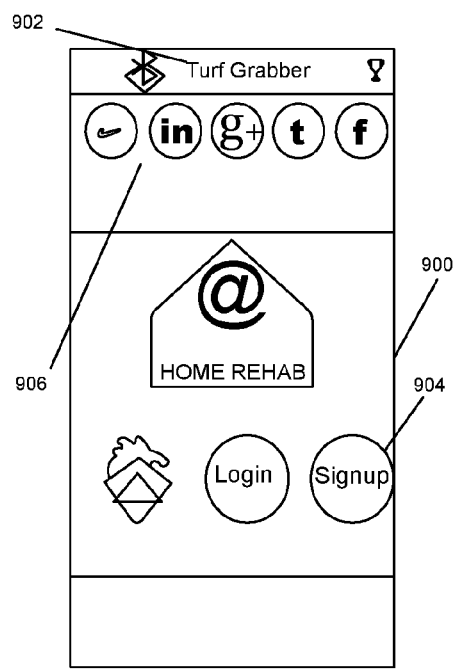
FIGS. 16A-K show the tracking system of the invention.
Figure 16B:
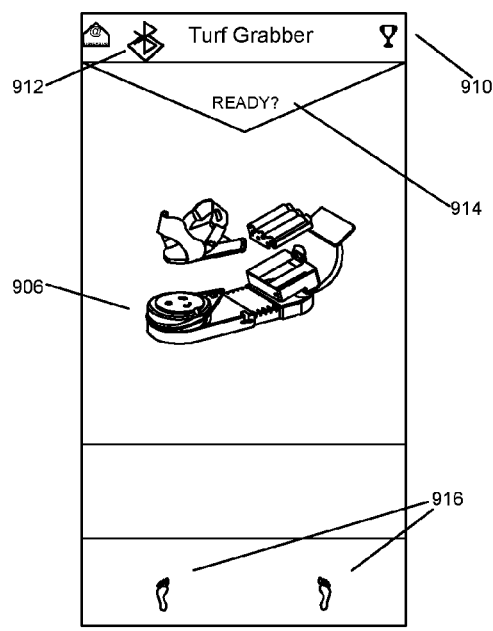

The mobile application 900 (FIG. 16A) is used to track the exercise device and display the user's progress. A home screen 902 provides login and sign up buttons 904 for users to create or choose their account. In addition, social media icons 906 represent the chance to connect or share exercise activity through a variety of social networks. Pressing the Bluetooth icon 912 connects the phone with the exercise device. This button can be a Bluetooth enabled button, but is not limited to solely Bluetooth. The capabilities are enabled for wireless, radio, Bluetooth, and a variety of capabilities. This must be done before beginning or choosing an exercise. An image of the device 908, FIG. 16B, remains at the center of the screen when beginning an exercise program.

Figures 16C, 16D:
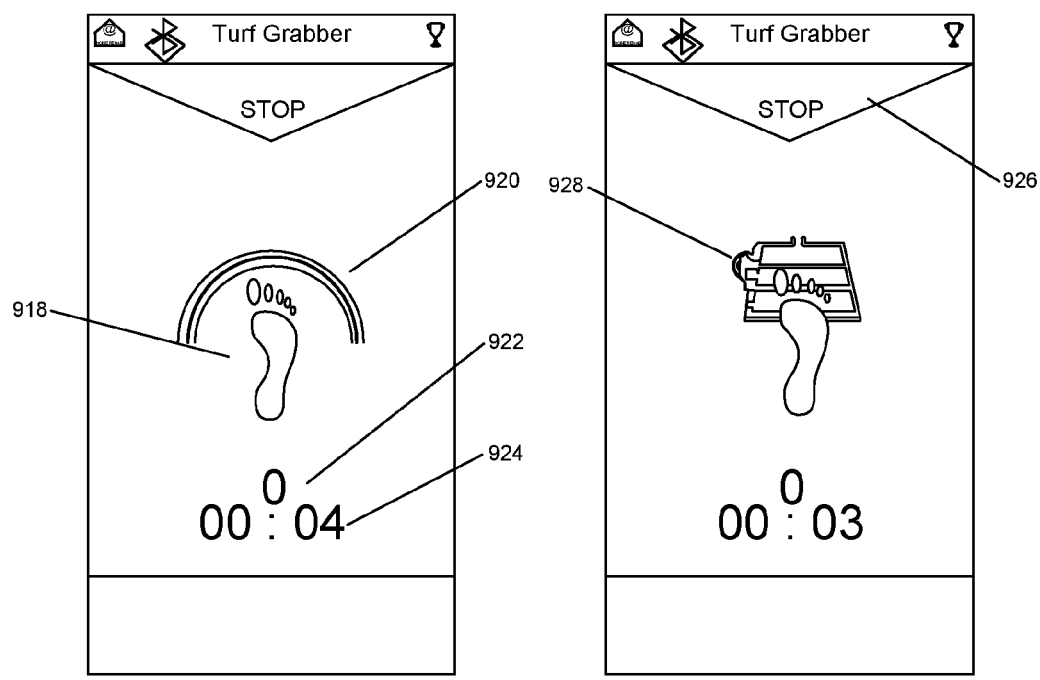
Figure 16E:
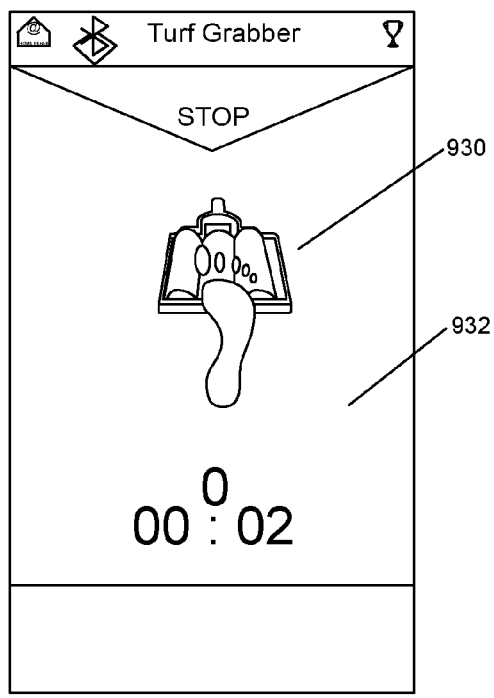
Figure 16F:
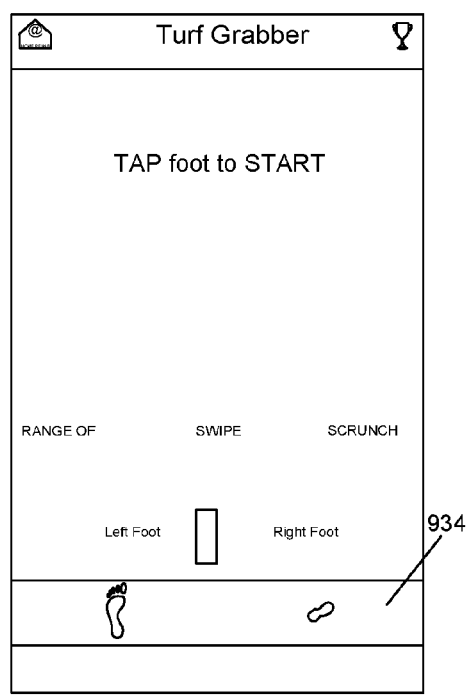
Figure 16G:
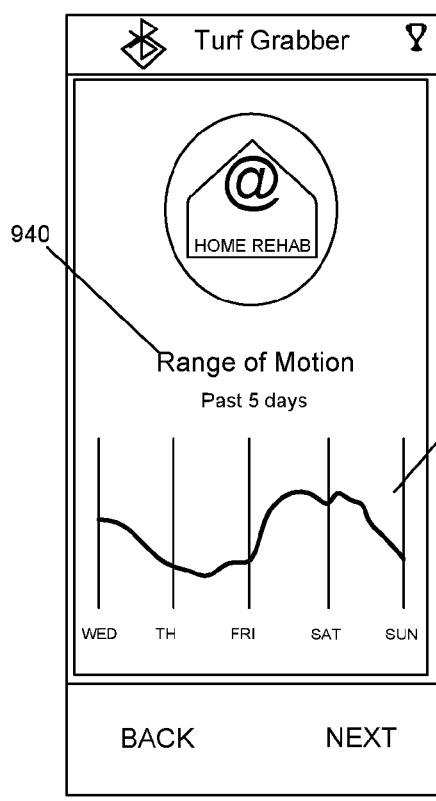
Figure 16H:
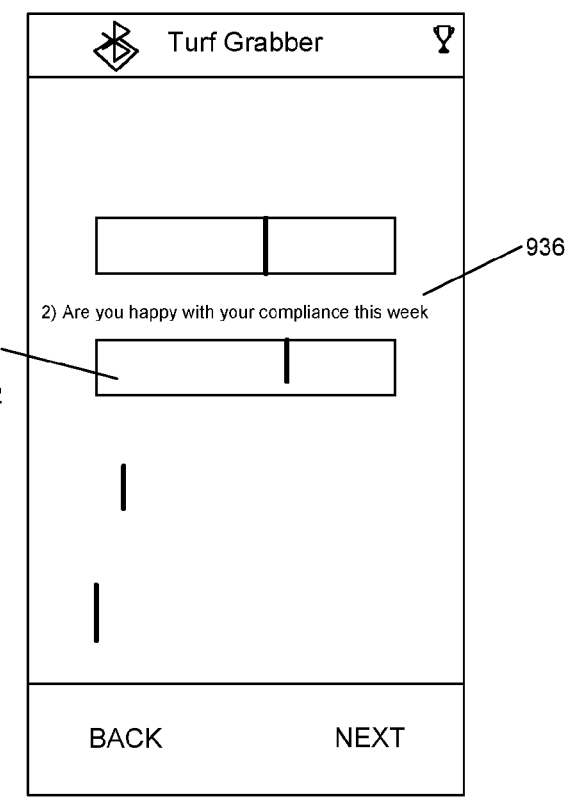
Figures 16I, 16J:
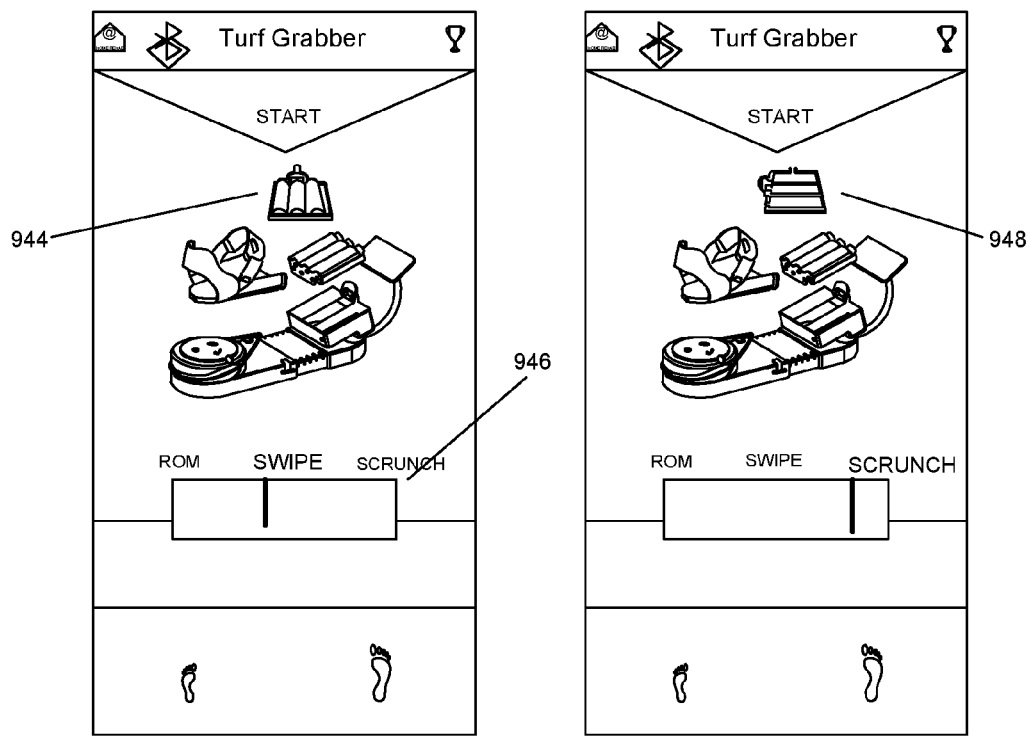
Figure 16K:
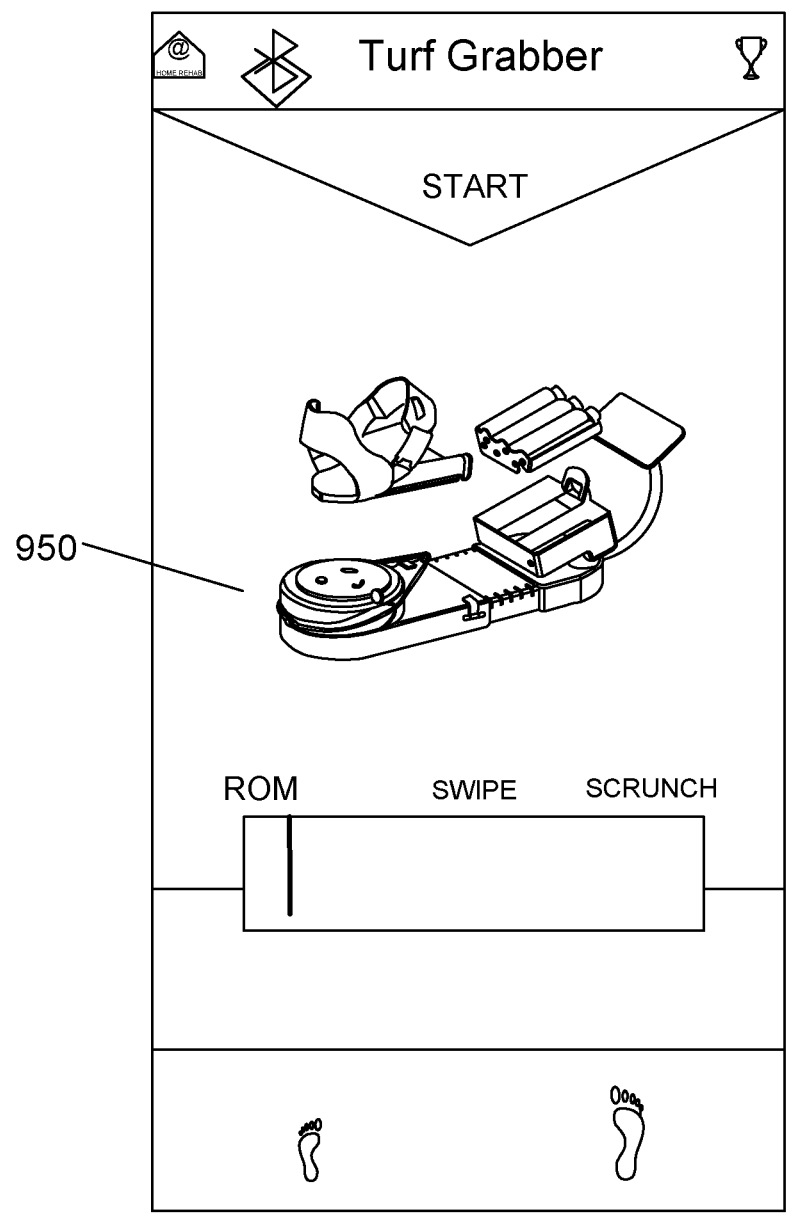

When the user is ready, pressing the distinct ready button 914 (FIG. 16B) allows them to choose between the exercise types and the feet icons 916 select between the left and right foot. This can also be utilized to designate between right and left hands and/or other anatomical landmarks that are being trained. The slider 946, FIG. 16I, allows the user to choose which exercise to perform to train. While choosing, additional images appear over (FIG. 16B) 908. Images of Swiping 944, FIG. 16I, Scrunching 948, FIG. 16J, and Rotation (Range Of Motion) (ROM) 950, FIG. 16K, are highlighted in such a way as to boldly stand out from (FIG. 16B) 908 when chosen. Long-pressing any inactive area of the screen (FIG. 16E) 932 opens the background selection menu. This menu provides the user to choose any background that they associate themselves with. The backgrounds range from a wide variety of sports and recreational activities containing, but not limited to: Baseball, Basketball, Football, Soccer, Tennis, Swimming, Golf, Bowling, Equestrian, Dance, and etc.

While exercising, a counter 922 (FIG. 16C) displays how many repetitions have been completed. Depending on which foot was chosen, the foot image (FIG. 16C) 918 will display a right or left foot. This image will be converted to any other anatomical landmarks that are being trained. During a ROM exercise, (FIG. 16C) 920 shows the progress towards completing a rep by expanding and changing color. This was fabricated to add a visual stimulus and positive reinforcement for the user to recognize if the repetition was satisfactory. The program has capabilities of setting conditions during the exercises to make the particular exercises more difficult. For example: If the user is within the "easy" range of motion 5-10 degrees of internal/external rotation would denote a "good-rep"; however if the user did not obtain a ROM of more than 5 degrees it would be a bad rep. Medium 10-15 for a "good-rep" and a Hard 20-30 for a "good-rep". These quantitative values for the settings can be varied for each user by either the user, programmer, or Medical Professional. In the case of scrunching, an image of the roller box (FIG. 16D) 928 shows the proper alignment of the device during this exercise associated with flexion and extension of the toes respectively. Finally, the roller box (FIG. 16E) 930 shows the alignment needed to perform swiping motions associated with Inversion, Eversion, Pronation, & Supination. For the purposes of the pictures provided feet and toes are described but any other anatomical landmarks that are being trained can be effectively used. The motions performed on the device are directly reflected on the mobile application screen. The data described is to be used as an assistive coaching method for Medical Professionals and also can be used as a self-coach method for users training at home.

While exercising, the timer (FIG. 16C) 924 shows elapsed time or time remaining to complete the workout. The start button also becomes a stop button (FIG. 16D) 926 so the user can quit the current activity. Other than the timed workouts, users can use the device and app as a controller for in-app gaming. When selecting a workout, a gaming icon (FIG. 16F) 934 brings the user to game selection. These games can be made available as rewards for completing prescribed exercises and turn the device into a controller. The games are directly linked up with the motion functions of the device. The device provides the user with an interactive platform that mimics the pre-determined motions completed by the user to gain form and function with the associated game. The controls of directional movements could theoretically be controlled by either: Swiping Left or Right, Scrunching, Rotating, and/or a combination of all three to effectively move the bar in the game. The gaming components are crucial for the design as they provide a fun, functional, and interactive approach towards training and rehabilitation. Future applications are being furthered researched, developed, and further patents will be filed.

The user can see their progress over time in the form of a line graph (FIG. 16G) 942 which shows the quality of a particular exercise 940 over a certain period. The results page or graphics associated to it are not limited to bar, line, info-graphics, pie, calendar charts, etc. FIG. 16H 936 displays Qualitative and Quantitative questioning programs utilizing Visual Analog Scales. This type of questioning is crucial to obtaining insightful information regarding the users training program. These types of questioning styles are shown by a slide bar 938. The slide bar is a way of finding relative information without enabling the user to use strict quantitative reasoning. Depending on where the user places the slide bar, that information is saved for further analysis and other purposes. It is noted that the operation of FIGS. 15-16 can be performed by the processing device of the system shown in FIG. 13, and is particularly implemented by the processing device of the mobile device of FIG. 13 and is displayed on the touch screen of the mobile device.

Figure 18:
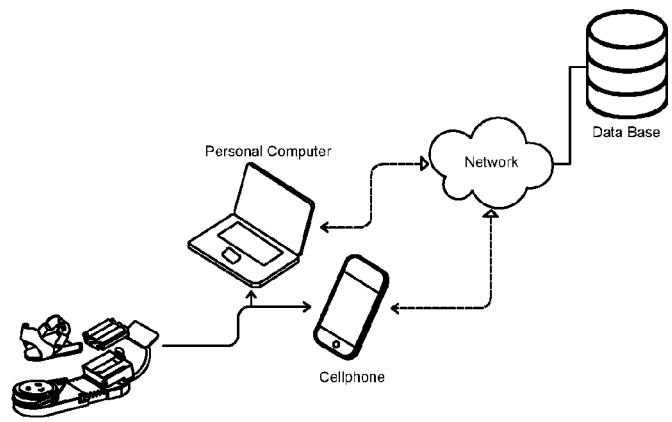
FIG. 18 shows the invention having a computer, phone and network.

FIG. 18 shows a flow diagram. It outlines the data flow from capture to storage. Using a wired or wireless utilizing but not limited to wifi, Bluetooth, and/or radiowaves) connection, a personal computer or cell phone pairs with the device to record exercise activity as data stored on the phone or computer. At a later point in time with an internet connection, the application securely uploads user data to a database for storage, authorized access, and analytics. A server with SQL capabilities would effectively sort and dispense user-specific data when queried by other software.

Accordingly, the tracking device 410 is utilized to track the movement of the foot receptacle 200 and/or the exercise system 300. A first sensor can be arranged to detect rotational motion of the foot receptacle, such as the degree, force (strength), and/or speed of rotation. A second sensor can be arranged to detect actuation of the exercise system 300. With respect to rollers, for instance, the sensor can detect the amount of rotation, the force (strength), and/or the speed of the rollers. The processing device of the tracking device 410 receives that information from the respective first and second sensors and determines an exercise characteristic based on the received information (the detected rotational motion and/or actuation). Exercise characteristics may include, for instance, calories burned, number of repetitions, degree of rotation (for the foot receptacle 200), duration of exercise, date/time. The tracking device 410 can also take into account the resistance level setting of the performed exercise.

In one non-limiting illustrative embodiment of the invention, the tracking device 410 can track the range of motion (degree of rotation) of the foot receptacle 200 over time to determine the user's progress for therapeutic or strength analysis by a physician or trainer. The tracking device 410 can further analyze the measurements for the foot receptacle 200 with respect to the measurements for the exercise/roller system 300. For instance, the device 410 can track the user's improvement with roller speed and determine if it is commensurate in scope with improvement of the foot receptacle 200, or determine an overall improvement measure based on both the movement of both the foot receptacle 200 and the rollers 350. Still further, the tracking device 410 can analyze these characteristics based in part on the pressure plate sensor. The device 410 can receive signals from pressure sensors in both of the foot receptacles 200 and determine if each foot is balanced, and can use the information from both sensors to determine if the user is balanced between both feet.

Tracking rotation and revolutions of the material triggers a tracking and counting device including but not limited to a combinations of sensors that are embedded within the edges of the proprioceptive material and the physical housing of the structure, sensors using magnetic, light sources, temperature principals. This counting and tracking device will track all but not limited to speed/velocity, revolutions/repetitions, force, pressure, magnitude, and time of the bout of exercises.

Open chained exercises can also be performed. Repetitions from regular exercises like Knee flexion and extension in addition to but not limited to having a sensor that will be similar to a sensor in a pedometer measuring the movement patterns of the user to measure start, during, and finishing phases of movement. The data collected serves as the quantitative measurement and once coupled with the qualitative assessments, the information will be uploaded for the practitioner and patient to see their progress Accordingly, the invention incorporates proprioceptive material 210 in an exercise device 10 that the user can use to perform AIS stretching. The invention includes use of a proprioceptive material sheet to lay on-top of the rollers to make a rolling pin like structure. This can provide a mini-treadmill for a person's fingers and toes. This rolling pin like structure provides a surface for the users to engage toe flexion/extension to either grab or flick the material. Instead of the treadmill being motorized, it would be activated by the person's movement. Grabbing would pull the material towards them and flicking would push the material away. The proprioceptive material allows the user to improve the dexterity and functionality of the fingers and toes while improving sensori-motor thus making improving morphological and neurophysiologic capacities within the body.

To train and re-educate a user's somatosensory proprioceptive neuromuscular (SPN) system by using an SPNRED material, the invention is able to challenge the user in a multitude of varying manners such as but not limited to; (1) varying materials, (2) strengthening and flexibility exercises (such as the open and closed chain activities discussed) that challenges multidimensional and planar movements, and (3) progressive resistance (by increasing the resistance tubing or band or rotation rate of scrunching, etc.). For (1), Varying Materials, organic and inorganic materials can be utilized as the proprioceptive material 210 and/or for the surface of the rollers 350, including but not limited to turf (Astro and Synthetic Grass) and fake plant replicas (IVY, MOSS, FLOWERS); Real Plants (moss, grass, shrubs, chia, etc. dried rice, beans, corn, barley, wheat, and other grains); Silicone and Rubber filaments like the Koosh ball is a toy ball made of rubber filaments (strings) attached to a soft rubber core, rubber bands, flexible silicone bristle units (silicone basting brush), toothbrush fibers, crushed up tires, rubber pellets; Metals, marbles, bullet casings, thimbles, diamond plating, stainless steel; Rubber/latex Tubing; gravel, stones, river rocks, marble, sand, sea-shells, sand paper, wood chips and sawdust; and clothing like material, animal skins, fur, human hair, faux animal fur, feathers, towels and carpet. All these can be used to fabricate grooved, smooth, rough, raised, and depressed somatosensory proprioceptive neuromuscular re-education material. However, other suitable material can be used as well. The materials 210 can have advertisements or print designs (such as team logos, a football or football field, etc.) applied via laser printing, silk screening, material based fabrication methods, adhesives, heat and or steam activated transfer of advertisements etc.

Figure 17:
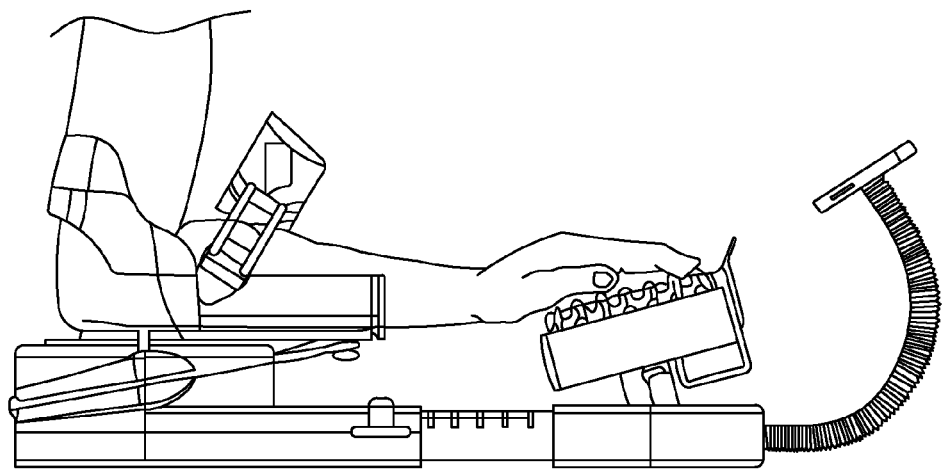
FIG. 17 shows the invention for use with a user's arm and hand.

Though the invention has been described in accordance with one or more preferred embodiments, it will be apparent that other suitable variations can be practiced within the spirit of the present invention. For instance, though the invention has been described and shown for use with a user's foot, it can also be configured for use with a user's arm/hand. As shown in FIG. 17, the user can place his/her arm in the receptacle 200 and move the rollers 350 with his/her fingers. The user can also position his/her hand in the receptacle 200. In addition, while the rollers 350 are configured to move to the left and right, the roller 350 can be rotated 90° so that the rollers 350 move up and down to enable a different exercise. The housing 310 and the frame 322 can be square, so that the roller cassette 320 can be rotated as desired. In addition, while rollers 350 are shown, other suitable variations include a flat surface that has a proprioceptive material such as turf, rocks, etc. Another variation includes the entire base 100 being mountable to the turntable 600 of FIG. 10. Still other variations are possible within the scope of the invention.

It will further be apparent that while the stimulation material 210 is used with the device 10 shown and illustrated, it can be provided with different exercise machines. For instance, the material 210, such as SPNRED material, can be provided on the running/walking surface of the bars of a weight-lifting device, the running/walking surface of a treadmill, or on the foot platforms of a stepping exercise machine. Still further, the stimulation material 210 can be used with other non-exercise devices, such as a standing padding used by people who stand in place for long periods of time to reduce the burden on the feet and legs, such as in the kitchen or in a work environment.

In addition, while the invention shows the use of rollers 350 in FIGS. 1-9, it will be apparent that other suitable elements can be provided for the exercise system 300 that need not have movement. For instance, the exercise system 300 can instead just be a flat platform (or with bumps or grooves or rounded) with SPNRED material (such as turf) that the user can use to perform toe exercises such as scrunching, swiping and/or rotating. Or, the exercise system 300 can be a combination of SPNRED material and rollers, such as placing the SPNRED material on the flat side portions 386 in FIGS. 8E, F, or the ramp 396 of FIG. 9A.

In another embodiment, a toe tube strengthening device is provided that has resistance such as but not limited to a pulley, tubing, rubber bands which is secured to the base of the exercise device. The mobile action of the digits is independent of each other and is focused on building eccentric strength within the toes and fingers. The ability to change the resistance could be used by increasing the tension via materials used, pulleys, cams, stronger or weaker tubing. This resistance is then attached to a five, individually ringed, molded material that allows the user to put either their fingers or toes within the rings. The securing system to the digits can be but is not limited to a ring, thimble, Toe Socks/Clothing material). The progressive resistance system serves as a way for the user to train their digits (fingers and toes). In addition, SPNRED material can be utilized with the toe ring.

In still a further embodiment, a conventional armband can be provided that optionally holds the Mobile Device 140 to the user's upper arm. A Kevlar pocket can be provided at the inside of the armband to retain SPNRED material in direct contact with the user's skin. The Arm Band provides a slot for the mobile device to be attached and secured directly to the arm. Behind the sport armband strap the material directly connected to the skin will use the same Somatosensory Proprioceptive Neuromuscular material. This will allow for easy access, update, and recognition of certain stretches, exercises, progression, quantitative and qualitative data upkeep. During exercise the device 410 assists the user to track their exercise results when doing aerobic activity. A Velcro attachment on the back of the armband will enable the user to secure the device directly to the exercise device if needed to track data utilizing gyroscope or pendulum like technology. In addition, while the invention is shown and described as being part of a portable device, it can be used on non-portable devices such as on the foot pedestal of a bike, elliptical or running machine.

The foregoing description and drawings should be considered as illustrative only of the principles of the invention. The invention may be configured in a variety of shapes and sizes and is not intended to be limited by the preferred embodiment. Numerous applications of the invention will readily occur to those skilled in the art. Therefore, it is not desired to limit the invention to the specific examples disclosed or the exact construction and operation shown and described. Rather, all suitable modifications and equivalents may be resorted to, falling within the scope of the invention.

The invention claimed is:

1. An exercise device comprising:
    a base;
    a platform rotatably coupled with said base, said platform having a somatosensory proprioceptive neuromuscular re-education (SPNRED) material, said SPNRED material providing stimulation to the user during exercise; and
    a resistance mechanism coupled to the base and the platform, said resistance mechanism resisting rotation of said platform with respect to said base.

2. The device of claim 1, wherein the SPNRED material comprises an artificial turf or rubber filaments.

3. The device of claim 1, wherein the SPNRED material provides re-education.

4. The device of claim 1, wherein said device is configured for user's skin to come into direct contact with the SPNRED material.

5. The device of claim 1, wherein said device is configured for a user's bare foot to come into direct contact with the SPNRED material.

6. The device of claim 5, wherein the user's toes can swipe, grab, flick, push and/or pull the SPNRED material.

7. The device of claim 1, further comprising a support and a roller coupled with the support.

8. The device of claim 1, wherein said device is portable.

9. The device of claim 1, wherein the exercise device comprises a cardiovascular machine.

10. The device of claim 9, wherein the exercise device comprises an elliptical machine, treadmill, or bicycle.

11. The device of claim 1, wherein said device can rotate.

12. The device of claim 1, further comprising a foot receptacle connected to said base, and further comprising a strap connected to said foot receptacle.

13. The device of claim 1, wherein the SPNRED material stimulates strength, stability, balance, and/or flexibility.

14. An exercise device comprising:
    a base;
    a foot receptacle rotatably mounted to said base; and
    an exercise element mounted to said base and aligned with said foot receptacle for actuation by a user's toes.

15. The device of claim 14, further comprising a somatosensory proprioceptive neuromuscular re-education (SPNRED) material coupled to said foot receptacle.

16. The device of claim 15, wherein the SPNRED stimulates the foot receptors during exercise.

17. The device of claim 15, further comprising somatosensory proprioceptive neuromuscular re-education (SPNRED) material coupled to said exercise element.

18. The device of claim 15, wherein said device provides therapeutic exercise.

19. The device of claim 14, further comprising a first sensor arranged to detect rotational motion of the foot receptacle, a second sensor arranged to detect actuation of said exercise element, and a processing device configured to receive information from said first and second sensors and determine an exercise characteristic based on the detected rotational motion and detected actuation.

* * * * *